US010925815B2

(12) United States Patent
Simonnet et al.

(10) Patent No.: US 10,925,815 B2
(45) Date of Patent: Feb. 23, 2021

(54) OIL-IN-WATER EMULSION COMPRISING AN AMPHIPHILIC POLYMER

(75) Inventors: Jean-Thierry Simonnet, Mamaroneck, NY (US); Florence L'Alloret, Paris (FR); Lydie Bressy, Villeurbanne (FR); Zohra Moujahed, Evry (FR)

(73) Assignee: L'OREAL, Paris (FR)

( * ) Notice: Subject to any disclaimer, the term of this patent is extended or adjusted under 35 U.S.C. 154(b) by 825 days.

(21) Appl. No.: 12/866,463

(22) PCT Filed: Feb. 11, 2009

(86) PCT No.: PCT/EP2009/051582
§ 371 (c)(1),
(2), (4) Date: Dec. 15, 2010

(87) PCT Pub. No.: WO2009/101113
PCT Pub. Date: Aug. 20, 2009

(65) Prior Publication Data
US 2011/0110989 A1    May 12, 2011

Related U.S. Application Data

(60) Provisional application No. 61/029,581, filed on Feb. 19, 2008.

(30) Foreign Application Priority Data

Feb. 12, 2008   (FR) ...................... 08 50881

(51) Int. Cl.
*A61K 8/06*   (2006.01)
*A61K 8/90*   (2006.01)
*A61Q 1/14*   (2006.01)
*A61K 8/87*   (2006.01)
*A61Q 19/00*  (2006.01)
*A61K 8/81*   (2006.01)

(52) U.S. Cl.
CPC ............... *A61K 8/06* (2013.01); *A61K 8/062* (2013.01); *A61K 8/8147* (2013.01); *A61K 8/8152* (2013.01); *A61K 8/8158* (2013.01); *A61K 8/87* (2013.01); *A61K 8/90* (2013.01); *A61Q 1/14* (2013.01); *A61Q 19/00* (2013.01); *A61K 2800/262* (2013.01)

(58) Field of Classification Search
None
See application file for complete search history.

(56) References Cited

U.S. PATENT DOCUMENTS 5,656,257 A    8/1997  Fealy et al.
6,228,348 B1   5/2001  Simon et al.
6,881,414 B2   4/2005  Chandar et al.
2003/0059392 A1  3/2003  L'Alloret
2003/0068291 A1  4/2003  Decoster et al.
2003/0157047 A1  8/2003  Lennon et al.
2004/0115148 A1  6/2004  Loffler et al.
2005/0002891 A1* 1/2005  Aubrun-Sonneville et al. ............ 424/70.17
2005/0053568 A1  3/2005  Aubrun-Sonneville et al.
2005/0191265 A1  9/2005  Seigneurin et al.
2006/0057097 A1  3/2006  Derici et al.
2006/0120982 A1  6/2006  Derici et al.

FOREIGN PATENT DOCUMENTS

| EP | 0 750 899 | 1/1997 |
|----|-----------|--------|
| EP | 1 279 398 | 1/2003 |
| EP | 1 462 094 | 9/2004 |
| FR | 2 853 544 | 10/2004 |
| JP | 2000-290459 A | 10/2000 |
| JP | 2003-073222 A | 3/2003 |
| JP | 2003-128532 A | 5/2003 |
| JP | 2004-315525 A | 11/2004 |
| JP | 2005-508286 A | 3/2005 |
| WO | WO 92/06669 A1 | 4/1992 |
| WO | WO 96/17591 A1 | 6/1996 |
| WO | WO 97/35543 A1 | 10/1997 |
| WO | 98 00494 | 1/1998 |
| WO | WO 99/09947 A1 | 3/1999 |
| WO | WO 99/09948 A1 | 3/1999 |
| WO | WO 99/09951 A1 | 3/1999 |
| WO | 02 43686 | 6/2002 |
| WO | WO 02/092043 A2 | 11/2002 |
| WO | WO 03/094874 A1 | 11/2003 |
| WO | WO 2006/065848 A1 | 6/2006 |
| WO | WO 2007/054824 A2 | 5/2007 |

(Continued)

OTHER PUBLICATIONS

International Search Report dated Nov. 19, 2010 in PCT/EP09/051582 filed Feb. 11, 2009.

(Continued)

*Primary Examiner* — Kevin E Weddington
(74) *Attorney, Agent, or Firm* — Oblon, McClelland, Maier & Neustadt, L.L.P.

(57) ABSTRACT

The present patent application relates to a composition for topical application in the form of an oil-in-water emulsion comprising an oily phase dispersed in an aqueous phase, characterized in that it comprises at least one noncrosslinked amphiphilic polymer, the globules of the said emulsion exhibiting a mean size ranging from 15 to 500 microns and the oily phase being present in an amount of less than 35% by weight, with respect to the total weight of the composition.

15 Claims, No Drawings

(56) References Cited

FOREIGN PATENT DOCUMENTS

WO     2009/101113     8/2009

OTHER PUBLICATIONS

English translation of the Office Action dated Nov. 19, 2013 in Japanese Patent Application No. 2010-546322.
"Latest Cosmetic Science" Saishin Keshohin Kagaku, Yakuji Nippo Limited, revised and enlarged edition II, Jul. 10, 1992, pp. 42-54.
Laura-Isabel Tolosa, et al. "Combined Effects of Formulations and Stirring on Emulsion Drop Size in the Vicinity of Three-Phase Behavior of Surfactant—Oil Water Systems," Ind. Eng. Chem. Res., vol. 45, No. 11, Apr. 21, 2006, pp. 3810-3814.
"Aculyn™ 22 Rheology Modifier/Stabilizer: A Very Efficient Thickener for Difficult to Thicken Surfactant Systems" DOW Personal Care Brochure, Sep. 2002, 12 Pages.
Eri Akiyama, et al. "Thickening properties and emulsification mechanisms of new derivatives of polysaccharides in aqueous solution" Journal of Colloid and Interface Sclience, vol. 282, 2005, pp. 448-457.
"Emulsifier Free Moisturizing Creme—Gel" R&D Personal Care, Clariant, vol. AVI/8733, Aug. 2002, 1 Page.
English Translation of Office Action dated Oct. 27, 2014 in Japanese Patent Application No. 2010-546322.
Office Action as received in the corresponcing Japanese Patent Applicaton No. 2015-039445 dated Mar. 28, 2016.

\* cited by examiner

OIL-IN-WATER EMULSION COMPRISING AN AMPHIPHILIC POLYMER The present patent application relates to a composition in the form of an oil-in-water emulsion comprising at least one specific amphiphilic polymer and to the use of the said composition, in particular for caring for, removing makeup from and/or cleaning the skin of the body or face, the hair, the lips and/or the eyes.

For various reasons related in particular to better comfort during use (softness, emollience and others), current cosmetic compositions are generally provided in the form of an emulsion of the oil-in-water (O/W) type composed of an aqueous dispersing continuous phase and of an oily dispersed noncontinuous phase or of an emulsion of the water-in-oil (W/O) type composed of an oily dispersing continuous phase and of an aqueous dispersed noncontinuous phase. W/O emulsions are the most in demand in the cosmetics field owing to the fact that they comprise, as external phase, an aqueous phase which confers thereon, during application to the skin, a fresher, less greasy and lighter feel than W/O emulsions.

Conventional O/W emulsions are generally stabilized by amphiphilic molecules of low molar mass (<5000 g/mol), such as emulsifying surfactants of glycerolated alkyl or polyoxyethylenated alkyl type. These emulsions generally exhibit a size of the oil drops or oily globules of the order of a micron. These oily globules thus strongly scatter light and the emulsion then exhibits a white colour.

Furthermore, emulsions based on polymers comprising a hydrophilic part and a hydrophobic part composed of a fatty chain, such as copolymers of $C_{10}$-$C_{30}$-alkyl acrylate and of acrylic or methacrylic acid, are known, such as the products sold under the name Pemulen TR1 and TR2 by Noveon. These crosslinked polymers result in emulsions comprising drops of larger size (of the order of 10-15 µm) which scatter light less than the emulsions having a drop size of the order of a micrometre and thus exhibit a more translucent appearance. However, these emulsions are difficult to stabilize in the case where it is desired to obtain fluid textures, as a phenomenon of creaming of the emulsion occurs.

The document FR-2 843 695 describes O/W emulsions comprising a noncrosslinked amphiphilic AMPS polymer and a level of oils of greater than 40% by weight. However, such an amount of oily phase produces a greasy and shiny effect during the application to the skin, which may be totally unacceptable for the user.

There thus exists a need to produce oil-in-water emulsions which exhibit a satisfactory translucent appearance, which give a nongreasy effect on the skin and which are stable whatever their viscosity and can thus be formulated within a broad range of textures (sprayable fluid to thick cream).

The Applicant Company has found, surprisingly, the possibility of producing oil-in-water emulsions comprising at least one noncrosslinked amphiphilic polymer and for which the mean size of the drops is between 15 et 500 µm which meets this need. The emulsions obtained are translucent and can be provided both in the form of fluids and of thick creams.

Thus, the present invention relates to a composition for topical application in the form of an oil-in-water emulsion comprising an oily phase dispersed in an aqueous phase, characterized in that it comprises at least one noncrosslinked amphiphilic polymer, the globules of the said emulsion exhibiting a mean size ranging from 15 to 500 microns and the oily phase being present in an amount of less than 35% by weight, with respect to the total weight of the composition.

In the present invention, the amount of oily phase does not include the amount of emulsifiers used according to the invention.

The term "topical application" is understood here to mean external application to keratinous substances, which are in particular the skin, scalp, eyelashes, eyebrows, nails, mucous membranes and hair.

As the composition according to the invention is intended for topical application, it comprises a physiologically acceptable medium, that is to say a medium compatible with keratinous substances, such as the skin, mucous membranes, keratinous fibres, such as the eyelashes or the hair, and the scalp.

The composition according to the invention exhibits the advantage of being satisfactorily harmless and of having good cosmetic properties, that is to say a homogeneous texture which is pleasant on application. In addition, it is very stable over time. An emulsion is stable if no change in its macroscopic or microscopic appearance and in its physicochemical characteristics (size of the drops, pH, viscosity) is observed after storing at ambient temperature for a time of 15 days.

The polymers used in the composition of the invention exhibit the advantage of making possible the dispersion of oils of any nature, both oils composed of triglycerides, on the one hand, and alkanes, esters, silicones, sunscreens or perfluorinated compounds, on the other hand, either alone or as mixtures.

In the present invention, the term "mean size of the oily globules" is understood to mean the volume-average "effective" diameter D[4,3] of the said globules, as measured by static light scattering using a commercial particle sizer of MasterSizer 2000 type from Malvern. The data are processed on the basis of the Mie scattering theory. This theory, exact for isotropic particles, makes it possible to determine, in the case of nonspherical particles, an "effective" particle diameter. This theory is described in particular in the work by Van de Hulst, H. C., "Light Scattering by Small Particles," chapters 9 and 10, Wiley, New York, 1957.

The volume-average "effective" diameter D[4,3] is defined in the following way:

$$D[4,3] = \frac{\sum_i V_i \cdot d_i}{\sum_i V_i}$$

where $V_i$ represents the volume of the particles with an effective diameter $d_i$. This parameter is described in particular in the technical documentation of the particle sizer.

The measurements are carried out at 25° C., after diluting the composition by a factor of greater than 100 using osmotically treated water.

The "effective" diameter is obtained by specifying the refractive indices of water and the fatty phase, depending on its nature.

The mean size of the oily globules can range from 15 to 500 µm, preferably from 15 to 300 µm and better still from 15 to 150 µm.

The emulsions according to the invention are translucent; in particular, they exhibit a transmission of light at a wavelength equal to 500 nm, through a sample with a thickness of 50 μm, which is at least 1.5 times greater than an emulsion with the same composition having a diameter for the drops of less than 15 μm.

The transmission is measured using a Carry 600 UV/visible spectrophotometer at a wavelength equal to 500 nm. The emulsion is placed between two quartz slides, one of which comprises a notch with a depth of 50 microns.

The viscosity of the dispersions obtained can range from very fluid (spray) to highly viscous (cream) and it is adjusted in particular according to the polymer content introduced and the level of emulsified oily phase. The composition of the invention exhibits a viscosity which can range, for example, from 0.01 Pa·s to 100 Pa·s at a temperature of 25° C., the viscosity being measured using a Rheomat 180 (Lamy), equipped with an MS-R1, MS-R2, MS-R3, MS-R4 or MS-R5 spindle, chosen according to the consistency of the composition, rotating at a rotational speed of 200 rev/min.

Amphiphilic Polymer

The term "amphiphilic polymer" is understood to mean a polymer which comprises at least a hydrophilic part (or block) and at least a hydrophobic part (or block). This polymer is water-soluble or water-dispersible.

The polymers of the invention can be block polymers or "comb" polymers which comprise, on the one hand, at least one water-soluble or water-dispersible polymer block and, on the other hand, at least one hydrophobic block.

The polymers employed in the context of the invention can thus be block (multiblock) polymers comprising, for example, water-soluble blocks alternating with hydrophobic blocks.

These polymers can also be provided in the form of grafted polymers, the backbone of which is composed of water-soluble or water-dispersible blocks and carries hydrophobic grafts, the backbone of the grafted polymers not being crosslinked.

The term "water-soluble or water-dispersible polymer" is understood to mean a polymer which, introduced into water at a concentration equal to 1%, results in a macroscopically homogeneous solution, the transmission of light of which, at a wavelength equal to 500 nm, through a sample with a thickness of 1 cm, is at least 10%, which corresponds to an absorbance [abs=−log(transmission)] of less than 1.5.

The term "amphiphilic polymer" is understood to mean a polymer which, introduced into aqueous solution at 0.05% (by weight), makes it possible to reduce the surface tension of the water at 25° C. to a value of less than 50 mN/m and preferably of less than 40 mN/m.

The polymers in accordance with the invention generally have a weight-average molar mass ranging from 10 000 to 10 000 000, more preferably from 50 000 to 8 000 000 and more preferably still from 100 000 to 3 000 000.

The amount (as active material) of amphiphilic polymer in the composition of the invention can range from 0.01% to 10% by weight, preferably from 0.05% to 5% by weight and better still from 0.1% to 3% by weight, with respect to the total weight of the composition.

The ratio of the amount of oily phase to the amount of polymer can range from 1 to 200 and preferably from 1 to 150.

A) Water-Soluble Polymer Blocks

The term "water-soluble blocks" is understood to mean blocks which, introduced into water at a concentration equal to 1%, result in a macroscopically homogeneous solution, the transmission of light of which, at a wavelength equal to 500 nm, through a sample with a thickness of 1 cm, is at least 10%, which corresponds to an absorbance [abs=−log(transmission)] of less than 1.5.

These water-soluble blocks can be obtained by radical polymerization of vinyl monomers or by polycondensation or also can be composed of existing natural or modified natural polymers.

Mention may be made, by way of example, of the following water-soluble monomers (a) and their salts which are capable of being employed to form the said water-soluble or water-dispersible blocks or units, alone or as mixtures:

(meth)acrylic acid,
vinylsulphonic acid and (meth)allylsulphonic acid,
vinylphosphonic acid,
methylvinylimidazolium chloride,
(meth)acrylamide,
2-vinylpyridine and 4-vinylpyridine,
maleic acid and maleic anhydride,
crotonic acid,
itaconic acid,
vinyl alcohol of formula $CH_2=CHOH$,
N-vinyllactams, such as N-vinylpyrrolidone, N-vinylcaprolactam and N-butyrolactam,
water-soluble styrene derivatives, in particular styrene-sulphonate,
dimethyldiallylammonium chloride,
N-vinylacetamide and N-methyl-N-vinylacetamide,
N-vinylformamide and N-methylvinylformamide,
water-soluble vinyl monomers of following formula (1):

in which:
R is chosen from H, —$CH_3$, —$C_2H_5$ or —$C_3H_7$
X is chosen from:
  alkyl oxides of type —OR' where R' is a saturated or unsaturated and linear or branched hydrocarbon radical having from 1 to 6 carbons, which is substituted by at least one halogen atom (iodine, bromine, chlorine or fluorine); one sulphonic (—$SO_3^-$), sulphate (—$SO_4^-$) or phosphate (—$PO_4H_2$) group; one hydroxyl (—OH) group; one ether (—O—) group; or one primary amine (—$NH_2$), secondary amine (—$NHR_1$), tertiary amine (—$NR_1R_2$) or quaternary amine (—$N^+R_1R_2R_3$) group with $R_1$, $R_2$ and $R_3$ being, independently of one another, a saturated or unsaturated and linear or branched hydrocarbon radical having from 1 to 6 carbon atoms, with the proviso that the sum of the carbon atoms of $R'+R_1+R_2+R_3$ does not exceed 7; mention may be made, for example, of quaternized dimethylaminoethyl methacrylate (DMAEMA), glycidyl (meth)acrylate, hydroxyethyl methacrylate and ethylene glycol, diethylene glycol or polyalkylene glycol (meth)acrylates,
—$NH_2$, —NHR' and —NR'R" groups in which R' and R" are, independently of one another, saturated or unsaturated and linear or branched hydrocarbon radicals having from 1 to 6 carbon atoms, with the proviso that the total number of carbon atoms of R'+R" does not exceed 7, the said R' and/or R" radicals being substituted by a halogen atom (iodine, bromine, chlorine, fluorine) or a hydroxyl (—OH), ether (—O—), sulphonic (—SO$_3^-$), sulphate (—SO$_4^-$), phosphate (—PO$_4$H$_2$), primary amine (—NH$_2$), secondary amine (—NHR$_1$), tertiary amine (—NR$_1$R$_2$) and/or quaternary amine (—N$^+$R$_1$R$_2$R$_3$) group with R$_1$, R$_2$ and R$_3$ being, independently of one another, a saturated or unsaturated and linear or branched hydrocarbon radical having from 1 to 6 carbon atoms, with the proviso that the sum of the carbon atoms of R'+R"+R$_1$+R$_2$+R$_3$ does not exceed 7; mention may be made, for example, of N,N-dimethylacrylamide, 2-acrylamido-2-methylpropanesulphonic acid (AMPS) or (meth)acrylamidopropyltrimethylammonium chloride (APTAC and MAPTAC).

The water-soluble blocks can comprise hydrophobic monomers (b), the said hydrophobic monomers being present in a sufficiently low amount for these units to be water-soluble.

Mention may be made, for example, as hydrophobic monomers (b), of:
  styrene and its derivatives, such as 4-butylstyrene, α-methylstyrene and vinyltoluene,
  vinyl acetate of formula CH$_2$=CH—OCOCH$_3$,
  vinyl ethers of formula CH$_2$=CHOR in which R is a saturated or unsaturated and linear or branched hydrocarbon radical having from 1 to 6 carbons;
  acrylonitrile,
  caprolactone,
  vinyl chloride and vinylidene chloride,
  silicone derivatives, such as methacryloyloxypropyltris(trimethylsiloxy)silane and silicone methacrylamides,
  hydrophobic vinyl monomers of following formula (2):

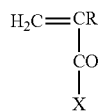

(2)

in which:
  R is chosen from H, —CH$_3$, —C$_2$H$_5$ or —C$_3$H$_7$,
  X is chosen from:
    alkyl oxides of —OR' type where R' is a saturated or unsaturated and linear or branched hydrocarbon radical having from 1 to 6 carbon atoms,
    —NH$_2$, —NHR' and —NR'R" groups in which R' and R" are, independently of one another, saturated or unsaturated and linear or branched hydrocarbon radicals having from 1 to 6 carbon atoms, with the proviso that the total number of carbon atoms of R'+R" does not exceed 6. Mention may be made, for example, of methyl methacrylate, ethyl methacrylate, n-butyl (meth)acrylate, tert-butyl (meth)acrylate, cyclohexyl acrylate, isobornyl acrylate and 2-ethylhexyl acrylate.

The water-soluble blocks may be unneutralized or else completely or partially neutralized by an inorganic or organic base. This base can be chosen, for example, from salts of sodium, ammonium, lithium, calcium, magnesium or ammonium substituted by 1 to 4 alkyl groups carrying from 1 to 15 carbon atoms or also from mono-, di- and triethanolamine, aminoethylpropanediol, N-methylglucamine, basic amino acids, such as arginine and lysine, and their mixtures.

Mention may be made, among polycondensates and natural or modified natural polymers capable of forming all or part of the water-soluble blocks, of:
  water-soluble polyurethanes,
  polyethyleneimine,
  polyethers, such as polyoxyethylenated and polyoxypropylene,
  xanthan gum, in particular that sold under the names Keltrol T and Keltrol SF by Kelco or Rhodigel SM and Rhodigel 200 by Rhodia;
  alginates (Kelcosol from Monsanto) and their derivatives, such as propylene glycol alginate (Kelcoloid LVF from Kelco);
  carrageenans of ι, κ and λ type,
  pectins with different degrees of modification (HM and LM),
  cellulose derivatives, in particular carboxymethylcellulose (Aquasorb A500, Hercules), hydroxymethylcellulose, hydroxypropylcellulose, hydroxypropylmethylcellulose, hydroxyethylcellulose and quaternized hydroxyethylcellulose;
  galactomannans and their derivatives, such as konjac gum, gellan gum, locust bean gum, fenugreek gum, karaya gum, gum tragacanth, gum arabic, acacia gum, guar gum, hydroxypropyl guar, hydroxypropyl guar modified by sodium carboxymethyl groups (Jaguar XC97-1, Rhodia) or hydroxypropyltrimethylammonium guar chloride,
  starch derivatives,
  and their mixtures.

The water-soluble polymer blocks have a molar mass of between 1000 g/mol and 10 000 000 g/mol when they constitute the water-soluble backbone of a comb polymer. These water-soluble blocks preferably have a molar mass of between 500 g/mol and 500 000 g/mol when they constitute a block of a multiblock polymer.

B) Hydrophobic Blocks

The term "hydrophobic blocks" is understood to mean blocks which are soluble or dispersible in fatty substances which are liquid at ambient temperature (25° C.) or oils, such as alkanes, esters, ethers, triglycerides, silicones or fluorinated compounds or a mixture of the abovementioned oils.

These blocks, introduced into an oil or an oily mixture at a concentration equal to 1% with stirring at 50° C. for 48 hours, result, after returning to ambient temperature, in a macroscopically homogeneous solution, the transmission of light of which, at a wavelength equal to 500 nm, through a sample with a thickness of 1 cm, is at least 10%, preferably at least 20%. The oil under consideration can be of alkane, ester, triglyceride, ether, silicone or fluorinated type or a mixture of the abovementioned oils.

Mention may be made, for example, of the hydrophobic blocks comprising at least:
  one alkyl radical comprising from 6 to 30 carbon atoms,
  one fluorinated or partially fluorinated C$_6$-C$_{30}$ alkyl radical (for example, the group of formula —(CH$_2$)$_2$—(CF$_2$)$_9$—CF$_3$),
  one cholesteryl radical or one radical derived from cholesterol (for example, cholesteryl hexanoate),
  one or more cyclic aromatic group(s), such as benzene, naphthalene or pyrene,
  one silicone or alkylsilicone or alternatively alkylfluorosilicone radical.

The molar mass of these hydrophobic blocks can be between 100 and 10 000 g/mol, preferably between 200 and 5000 g/mol.

The proportion by weight of the hydrophobic blocks in the final amphiphilic polymer is preferably between 1% and 60% by weight, in particular between 2% and 40% by weight, and particularly between 5% and 30% by weight, with respect to the final polymer.

Preparation of the Amphiphilic Polymers

The polymers employed in the context of the invention can be easily prepared according to various methods, including, for example:

For the "Comb" Polymers:
  Copolymerization: One possibility for preparing "comb" polymers consists in copolymerizing, for example, a macromonomer comprising a hydrophobic block (hydrophobic block described above with a vinyl end) and a water-soluble vinyl monomer, such as acrylic acid or the vinyl monomers having the formula (1).
  Grafting: Another possibility consists in grafting hydrophobic blocks having at least one reactive end to a water-soluble polymer comprising complementary reactive sites.

For the Block Polymers:
  Coupling reaction: When the final polymer is provided in the form of a block polymer, it is possible to prepare it by coupling between water-soluble blocks and hydrophobic blocks having complementary reactive sites at each end.
  Living polymerization: It is possible to prepare the polymers of the invention by living polymerization of anionic or cationic type, or else by controlled radical polymerization. The latter synthetic process can be employed according to various processes, such as, for example, the route by atom transfer (Atom Transfer Radical Polymerization or ATRP), the method involving radicals, such as nitroxides, or the route via Reversible Addition-Fragmentation Chain Transfer, such as the MADIX (Macromolecular Design via the Interchange of Xanthate) process. These synthetic processes can be used to obtain the water-soluble blocks and the hydrophobic blocks of the polymers of the invention; they can also be used to synthesize just one of the two types of blocks of the polymer of the invention, the other block being introduced into the final polymer via the initiator used or else by the coupling reaction between the water-soluble and hydrophobic blocks.

The amphiphilic polymers which can be used in the composition according to the invention can be chosen in particular from:

1) Polymers Derived from 2-acrylamido-2-methylpropanesulphonic Acid (AMPS)

Mention may be made of amphiphilic polymers comprising:
(a) from 80 to 99 mol % of 2-acrylamido-2-methylpropanesulphonic acid (AMPS) unit of following formula (3):

$$\begin{array}{c} -CH_2-CH- \\ | \\ O=C \quad CH_3 \\ | \quad | \\ NH-C-CH_2SO_3^-X^+ \\ | \\ CH_3 \end{array} \quad (3)$$

in which $X^+$ is a proton, an alkali metal cation, an alkaline earth metal cation or the ammonium ion;

(b) and from 1 to 20 mol %, preferably from 1 to 15 mol %, of unit of following formula (3a):

$$\begin{array}{c} R_1 \\ | \\ -CH_2-C- \\ | \\ O=C \\ | \\ O-(CH_2CH_2O)_n-(CH_2CH(CH_3)O)_p-R_3 \end{array} \quad (3a)$$

in which n and p denote, independently of one another, a number of moles and vary from 0 to 30, preferably from 1 to 20, with the proviso that n+p is less than or equal to 30, preferably less than 25 and better still less than 20; $R_1$ denotes a hydrogen atom or a linear or branched $C_1$-$C_6$ alkyl (preferably methyl) radical and $R_3$ denotes a linear or branched alkyl group comprising m carbon atoms ranging from 6 to 30, preferably from 10 to 25.

These polymers in accordance with the invention are preferably partially or completely neutralized by an inorganic base (for example sodium hydroxide, potassium hydroxide or ammonia) or an organic base, such as mono-, di- and triethanolamine, aminomethylpropanediol, N-methylglucamine, basic amino acids, such as arginine and lysine, and their mixtures.

The amphiphilic AMPS polymers used in the composition according to the invention are noncrosslinked.

They can be obtained according to conventional radical polymerization processes in the presence of one or more initiators, such as, for example, azobisisobutyronitrile (AIBN), azobisdimethylvaleronitrile, 2,2'-azobis[2-amidinopropane]hydrochloride (ABAH), organic peroxides, such as dilauryl peroxide, benzoyl peroxide, tert-butyl hydroperoxide, and the like, inorganic peroxide compounds, such as potassium persulphate or ammonium persulphate, or $H_2O_2$, optionally in the presence of reducing agents.

The polymers are obtained in particular by radical polymerization in a tert-butanol medium from which they precipitate. It is possible, by using polymerization in tert-butanol, to obtain a distribution in the size of the polymer particles which is particularly favourable for the uses of the polymer.

The polymerization reaction can be carried out at a temperature of between 0° C. and 150° C., preferably between 20° C. and 100° C., either at atmospheric pressure or under reduced pressure. It can also be carried out under an inert atmosphere, preferably under nitrogen.

Mention may in particular be made, as polymers derived from AMPS which can be used in the composition according to the invention, of the polymers prepared from 2-acrylamido-2-methylpropanesulphonic acid (AMPS) or one of its sodium or ammonium salts with an ester of (meth)acrylic acid and:
  of a $C_{10}$-$C_{18}$ alcohol oxyethylenated with 8 mol of ethylene oxide (Genapol C-080 from Clariant),
  of a $C_{11}$ oxo alcohol oxyethylenated with 8 mol of ethylene oxide (Genapol UD-080 from Clariant),
  of a $C_{11}$ oxo alcohol oxyethylenated with 7 mol of ethylene oxide (Genapol UD-070 from Clariant),
  of a $C_{12}$-$C_{14}$ alcohol oxyethylenated with 7 mol of ethylene oxide (Genapol LA-070 from Clariant),
  of a $C_{12}$-$C_{14}$ alcohol oxyethylenated with 9 mol of ethylene oxide (Genapol LA-090 from Clariant), of a $C_{12}$-$C_{14}$ alcohol oxyethylenated with 11 mol of ethylene oxide (Genapol LA-110 from Clariant),
of a $C_{16}$-$C_{18}$ alcohol oxyethylenated with 8 mol of ethylene oxide (Genapol T-080 from Clariant),
of a $C_{16}$-$C_{18}$ alcohol oxyethylenated with 11 mol of ethylene oxide (Genapol T-110 from Clariant),
of a $C_{16}$-$C_{18}$ alcohol oxyethylenated with 15 mol of ethylene oxide (Genapol T-150 from Clariant),
of a $C_{16}$-$C_{18}$ alcohol oxyethylenated with 20 mol of ethylene oxide (Genapol T-200 from Clariant),
of a $C_{16}$-$C_{18}$ alcohol oxyethylenated with 25 mol of ethylene oxide (Genapol T-250 from Clariant),
of a $C_{18}$-$C_{22}$ alcohol oxyethylenated with 25 mol of ethylene oxide,
of a $C_{16}$-$C_{18}$ iso alcohol oxyethylenated with 25 mol of ethylene oxide.

According to a preferred embodiment, the amphiphilic polymer is a copolymer of AMPS and of a methacrylate of a $C_{16}$-$C_{18}$ alcohol comprising from 6 to 25 oxyethylene groups obtained from methacrylic acid or from a methacrylic acid salt and from a $C_{16}$-$C_{18}$ alcohol oxyethylenated with 6 to 25 mol of ethylene oxide. The amphiphilic polymer can also be a copolymer of AMPS and of a methacrylate of a $C_{12}$-$C_{14}$ alcohol comprising from 6 to 25 oxyethylene groups obtained from methacrylic acid or from a methacrylic acid salt and from a $C_{12}$-$C_{14}$ alcohol oxyethylenated with 6 to 25 mol of ethylene oxide.

Mention may be made, as amphiphilic polymers preferred according to the present invention, of:
the noncrosslinked copolymer obtained from 92.65 mol % of AMPS and 7.35 mol % of a methacrylate of a $C_{16}$-$C_{18}$ alcohol comprising 8 oxyethylene groups (Genapol T-080), such as that sold by Clariant under the name Aristoflex SNC,
the noncrosslinked copolymer obtained from 91.5 mol % of AMPS and 8.5 mol % of a methacrylate of a $C_{12}$-$C_{14}$ alcohol comprising 7 oxyethylene groups (Genapol LA-070), such as that sold by Clariant under the name Aristoflex LNC,
and their blends.

These copolymers are appropriate for giving stable emulsions which are provided under highly varied textures, ranging from sprayable fluid to cream, with very good cosmetic qualities.

These polymers exhibit the advantage of being relatively insensitive to pH variations for values of between 4 and 8, which are the normal values of cosmetic compositions.

The amphiphilic polymers derived from AMPS can exhibit a weight-average molar mass ranging from 50 000 to 10 000 000, more preferably from 100 000 to 8 000 000 and more preferably still from 200 000 to 3 000 000.

The amount (as active material) of amphiphilic polymer based on AMPS can range in particular from 0.1 to 1.5% by weight, with respect to the total weight of the composition according to the invention.

2) Polymers Derived from (Meth)Acrylic Acid

Mention may be made of the amphiphilic polymers comprising:
(a) from 80 to 99 mol % of acrylic acid (AA) unit of following formula (4):

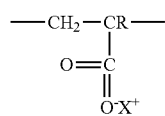

(4)

in which R is H or $CH_3$ and $X^+$ is a proton, an alkali metal cation, an alkaline earth metal cation or the ammonium ion;
(b) and from 1 to 20 mol %, preferably from 1 to 15 mol %, of unit of following formula (5):

(5)

in which:
$R_1$ denotes a hydrogen atom or a linear or branched $C_1$-$C_6$ alkyl (preferably methyl) radical,
A denotes an ester or amide group or an oxygen atom, and
$R_4$ denotes a linear or branched alkyl comprising a number of carbon atoms ranging from 6 to 30, preferably from 10 to 25.

The amphiphilic polymers derived from (meth)acrylic acid can exhibit a weight-average molar mass ranging from 50 000 to 10 000 000, more preferably from 100 000 to 8 000 000 and more preferably still from 200 000 to 3 000 000.

These polymers are partially or completely neutralized by an inorganic base (for example sodium hydroxide, potassium hydroxide or ammonia) or an organic base, such as mono-, di- and triethanolamine, an aminomethylpropanediol, N-methylglucamine, basic amino acids, such as arginine and lysine, and their mixtures.

These amphiphilic polymers derived from (meth)acrylic acid according to the invention are noncrosslinked.

Mention may be made, as preferred amphiphilic polymers derived from (meth)acrylic acid, of:
the noncrosslinked copolymer obtained from (meth) acrylic acid and steareth-20 methacrylate sold under the name Aculyn 22 by Röhm & Haas,
the noncrosslinked copolymer obtained from (meth) acrylic acid and laureth-25 methacrylate sold under the name Aculyn 25 by Röhm & Haas,
the noncrosslinked copolymer obtained from (meth) acrylic acid and beheneth-25 methacrylate sold under the name Aculyn 28 by Röhm & Haas,
the noncrosslinked copolymer obtained from (meth) acrylic acid and steareth-20 itaconate sold under the name Structure 2001 by National Starch,
the noncrosslinked copolymer obtained from (meth) acrylic acid and ceteth-20 itaconate sold under the name Structure 3001 by National Starch,
the noncrosslinked copolymer obtained from (meth) acrylic acid, aminoacrylate and $C_{10}$-$C_{30}$ alkyl PEG 20 itaconate sold under the name Structure Plus by National Starch,
the noncrosslinked copolymer obtained from (meth) acrylic acid, methyl acrylate and dimethyl-meta-isopropenylbenzyl isocyanate of ethoxylated alcohol sold under the name Viscophobe DB 1000 by Amerchol.

The amount (as active material) of amphiphilic polymer based on (meth)acrylic acid can range in particular from 0.5 to 5% by weight, with respect to the total weight of the composition.

3) Block Copolymers, in Particular Diblock Copolymers, Based on (Poly)Styrene

These copolymers are advantageously (block A)-(block B) diblock copolymers in which
the block A comprises at least units deriving from styrene;

the block B comprises (a) at least units deriving from acrylic acid in the free or salified form and (b) at least units deriving from a $C_1$-$C_4$ alkyl acrylate.

These block copolymers, preferably diblock copolymers, are advantageously linear.

More preferably, the proportion by weight of the block B with respect to the copolymer is greater than or equal to 50%.

The diblock copolymers which can be used in the composition according to the invention are more particularly characterized in that they are (block A)-(block B) diblock copolymers in which:

the block A comprises at least 90% by weight of units deriving from styrene, with respect to the total weight of the block A;

the block B is a random block comprising, with respect to the total weight of the block B:

(i) from 34 to 95% by weight of units deriving from acrylic acid in the acid form or in the salified form;

(ii) from 5 to 66% by weight of units deriving from $C_1$-$C_4$ alkyl acrylate.

In the present patent application, the term "diblock copolymer" relates to an architecture formed of a block copolymer composed of two blocks which does not substantially exhibit another sequence of blocks.

In the present patent application, the term "unit deriving from a monomer" denotes a unit which can be obtained directly from the said monomer by polymerization. Thus, for example, a unit deriving from an acrylic or methacrylic acid ester does not cover a unit of formula —$CH_2$—CH(COOH)— or —$CH_2$—C($CH_3$)(COOH)— obtained, for example, by polymerizing an acrylic or methacrylic acid ester and by then hydrolysing. Thus, the terminology "unit deriving from a monomer" relates only to the final structure of the polymer and is independent of the polymerization process used to synthesize the polymer.

The ratio by weight between the blocks corresponds to the ratio between the weights of the monomers (or mixtures of monomers) used for the preparation of the blocks (taking into account the variations in weight related to a subsequent hydrolysis). The proportions by weight of the blocks are the proportions with respect to the complete diblock copolymer and correspond to the proportions by weight of the monomers (or mixtures of monomers) used for the preparation of the blocks, with respect to all the monomers used to prepare the diblock copolymer (taking into account the variations in weight related to the subsequent hydrolysis).

The weights and ratios related to the blocks are shown as acid equivalents (units deriving from acrylic acid in the acid form, in contrast to a salt form of sodium acrylate type).

Preferably, the $C_1$-$C_4$ alkyl acrylate monomer is ethyl acrylate.

According to a preferred form of the invention, the block A and/or the block B comprises up to 10% by weight (in particular from 0.1% to 10% by weight) and preferably up to 5% by weight (in particular from 0.1% to 5% by weight) of an additional, ionic or nonionic, hydrophilic comonomer, with respect to the weight of the block A or of the block B comprising the said hydrophilic monomer.

The term "hydrophilic monomer" is understood to mean a monomer which has an affinity for water and which typically is not capable of forming a macroscopic two-phase solution in distilled water at 25° C. at a concentration of 1% by weight.

Mention may be made, among the additional, ionic or nonionic, hydrophilic comonomers, for example, of acrylamide, hydroxyethyl (meth)acrylate, methacrylic acid (AMA) and their salts. It is more particularly preferable to use methacrylic acid or one of its salts. The block A can also comprise, as additional hydrophilic monomer, acrylic acid and its salts.

A first family of diblock copolymers in accordance with the invention which is particularly preferred is composed of (block A)-(block B) diblock copolymers of type (1) in which the proportion by weight of the block B with respect to the copolymer is between 50 and 85% and preferably between 50 and 75%.

A second family of diblock copolymers in accordance with the invention which is particularly preferred is composed of (block A)-(block B) diblock copolymers of the type (2) in which the proportion by weight of the block B with respect to the copolymer is greater than or equal to 85%.

Two types of copolymers are advantageously distinguished among these diblock copolymers of type (2):

Type (2a): where the proportion by weight of the block B with respect to the copolymer is greater than or equal to 87%, in particular greater than or equal to 87% and less than 94%.

Type (2b): where the proportion by weight of the block B with respect to the copolymer is greater than or equal to 94%, in particular ranging from 94% to 97%.

Two types of copolymers are advantageously distinguished among these diblock copolymers of type (2a):

Type (2a1): where, in the block B:

the proportion by weight of units deriving from acrylic acid in the free or salified form is between 64% (obtained, for example, by one of hydrolysis to a degree of T=0.7) and 75% (obtained, for example, by one of hydrolysis to a degree of T=0.8), and the proportion by weight of units deriving from $C_1$-$C_4$ alkyl acrylate is between 25% (obtained, for example, by one of hydrolysis to a degree of T=0.8) and 36% (obtained, for example, by one of hydrolysis to a degree of T=0.7).

Type (2a2): where, in the block B:

the proportion by weight of units deriving from acrylic acid in the free or salified form is between 75% (obtained, for example, by one of hydrolysis to a degree of T=0.8) and 95% (obtained, for example, by one of hydrolysis to a degree of T=0.96), and the proportion by weight of units deriving from $C_1$-$C_4$ alkyl acrylate is between 5% (obtained, for example, by one of hydrolysis to a degree of T=0.96) and 25% (obtained, for example, by one of hydrolysis to a degree of T=0.8).

The (block A)-(block B) diblock copolymers used in the context of the invention can be obtained by a process comprising the following stages:

I) a (block A)-(block B') diblock copolymer is prepared by a process comprising the following intermediate stages Ia) and Ib):

Ia) a first block A is prepared by bringing together:

$n_T$ mol of a transfer agent comprising a single transfer group, $n_A$ mol of styrene or of a mixture of monomers comprising at least 90% by weight of styrene and where $n_A/n_T>5$ and preferably <5000;

and optionally a free radical initiator,

Ib) a second block B' is prepared in order to obtain a (block A)-(block B') diblock copolymer by bringing together:

the block A obtained in the preceding stage, $n_B$ mol of a $C_1$-$C_4$ alkyl acrylate or of a mixture of monomers comprising at least 90% by weight of a $C_1$-$C_4$ alkyl acrylate so that $n_B/n_T>5$ and preferably <5000;

and optionally a free radical initiator,

II) the block B' is subsequently hydrolysed to a degree T in moles of between 0.4 and 0.96 in order to obtain the said (block A)-(block B) diblock copolymer, III) optionally, during and/or after stage II), transfer groups carried by macromolecular chains are deactivated and/or the (block A)-(block B) diblock copolymer is purified and/or hydrolysis and/or deactivation by-products are destroyed and, preferably:

T is between 0.4 and 0.96, preferably between 0.7 and 0.8, preferably approximately 0.75 or approximately 0.90, $n_A/n_T>5$ and preferably $n_A/n_T<5000$, $n_B/n_T>5$ and preferably $n_B/n_T<5000$.

However, the terminologies of the (block A)-(block B') type do not exclude the presence of chemical groups of use (transfer groups or residues) for the polymerization, in particular at chain ends. Thus, the diblock copolymer can in reality exhibit a formula of the R-(block A)-(block B')-X type (for example, X is a transfer group of formula —S—CS—Z or a residue of such a group).

In the present patent application, the degree of hydrolysis T is defined as the ratio of the number of units deriving from acrylic acid or an acrylic acid salt to the number of units deriving from $C_1$-$C_4$ alkyl acrylate which are present in a copolymer before hydrolysis. The number of units deriving from $C_1$-$C_4$ alkyl acrylate is regarded as being equal to the amount by number of alkyl acrylate monomer used for the preparation of the copolymer. The number of units deriving from acrylic acid or from an acrylic acid salt can be determined by any known method, in particular by potentiometric acid/base titration of the number of —COONa groups using a strong acid, for example using hydrochloric acid.

In the present patent application, the molar mass $M_A$ of a mixture of monomers $A_1$ and $A_2$ with respective molar masses of $M_A$, and $M_{A2}$, present in respective numbers of $n_{A1}$ and $n_{A2}$, denotes the number-average molar mass $M_A = M_{A1} \ n_{A1}/(n_{A1}+n_{A2}) + M_{A2} \ n_{A2}/(n_{A1}+n_{A2})$. The molar mass of a mixture of units in a macromolecular chain or a portion of a macromolecular chain (for example a block) is defined in the same way, with the molar masses of each of the units and the number of each of the units.

In the present patent application, the measured average molecular weight of a first block or of a copolymer denotes the number-average molecular weight as polystyrene equivalents of a block or of a copolymer, measured by steric exclusion chromatography (SEC), in THF, with calibration using polystyrene standards. The measured average molecular weight of an actual block in a copolymer comprising n blocks is defined as the difference between the measured average molecular weight of the copolymer and the measured average molecular weight of the copolymer comprising (n−1) blocks from which it is prepared.

In the present patent application, the term "transfer agent" is understood to mean an agent capable of bringing about controlled radical polymerization in the presence of unsaturated monomers and optionally of a source of free radicals. Such agents are known to a person skilled in the art and include in particular compounds comprising an —S—CS— transfer group for the implementation of polymerization processes known under the terms of RAFT and/or MADIX. Such processes and agents are explained in detail later.

The polymerization process as described above is described in particular in the document WO 01/16187.

During stage I) described above, it is possible to carry out the preparation of a first block from monomers or a mixture of monomers, from initiators and/or from agents which promote the control of the polymerization (transfer agents comprising —S—CS— or nitroxide groups, and the like) and then the growth of a second block on the first block in order to obtain a diblock copolymer with different monomers from those used for the preparation of the preceding block, and optionally with addition of initiators and/or of agents which promote the control of the polymerization. These processes for the preparation of block copolymers are known to a person skilled in the art. It is mentioned that the copolymer can exhibit, at a chain end, a transfer group or a residue of a transfer group, for example a group comprising an —S—CS— group (for example resulting from a xanthate or from a dithioester) or a residue of such a group.

During stage II), the units deriving from the hydrolysable monomers of the block B' are partially hydrolysed to form a block B comprising units deriving from acrylic acid or from a salt (hydrolysed units) and units deriving from the alkyl acrylate monomer (nonhydrolysed units). These two types of units are distributed randomly in the block B; the block B can thus be regarded as a block in the form of a random copolymer comprising units deriving from alkyl acrylate and units deriving from acrylic acid or from an acrylic acid salt. Naturally, the block B can comprise other units, in minimum amounts, if a mixture of monomers is used during the implementation of stage Ib).

The block A comprises units deriving from styrene. The block A can be obtained from a mixture of monomers comprising at least 90% by weight, preferably at least 95% by weight, of styrene ("St") and a hydrophilic comonomer or several hydrophilic comonomers. The block A can thus be a random copolymer comprising at least 90% by weight (in particular from 90% to 99.9% by weight), preferably at least 95% by weight (in particular from 95% to 99.9% by weight), of units deriving from styrene and up to 10% by weight (in particular from 0.1% to 10% by weight), preferably up to 5% by weight (in particular from 0.1% to 5% by weight), of other units deriving from hydrophilic comonomer(s).

The block B' comprises units deriving from a $C_1$-$C_4$ alkyl acrylate. The block B' can be obtained from a mixture of monomers comprising at least 90% by weight (in particular from 90% to 99.9% by weight), preferably at least 95% by weight (in particular from 95% to 99.9% by weight), of a $C_1$-$C_4$ alkyl acrylate and one or more hydrophilic comonomer(s). The block B' can thus be a random copolymer comprising at least 90% by weight (in particular from 90% to 99.9% by weight), preferably at least 95% by weight (in particular from 95% to 99.9% by weight), of units deriving from the $C_1$-$C_4$ alkyl acrylate and up to 10% by weight (in particular from 0.1% to 10% by weight), preferably up to 5% by weight (in particular from 0.1% to 5% by weight), of other units deriving from hydrophilic comonomer(s).

The block B obtained from the block B' after hydrolysis comprises units deriving from the hydrolysable $C_1$-$C_4$ alkyl acrylate, units deriving from acrylic acid or a salt and optionally units deriving from a hydrophilic comonomer employed during stage Ib) of growth of the block B', for example units deriving from acrylic acid. The acrylic acid is generally present in the block B in the form of a salt. This form generally results from the conditions for implementing the hydrolysis and from the reactants used. An alkali metal salt, such as a sodium salt or a potassium salt, is generally involved. Consequently, the block B generally comprises units deriving from acrylic acid in the form of sodium acrylate or potassium acrylate.

Mention is made, among the hydrophilic comonomer(s) which can be of use in the preparation of the block A and/or of the block B', of hydrophilic comonomer(s) capable of stabilizing an emulsion of monomers and/or of stabilizing the polymer obtained by emulsion polymerization. Mention may in particular be made of ionic or nonionic hydrophilic comonomers, such as acrylamide, hydroxyethyl (meth)acrylate, methacrylic acid (MAA) and their salts. It is preferable to use methacrylic acid or its salts. Methacrylic acid is not sensitive to hydrolysis. However, it can be salified during the hydrolysis. Use may also be made, as hydrophilic comonomer, for the preparation of the block A, of acrylic acid and its salts.

Mention is in particular made, among hydrolysable $C_1$-$C_4$ alkyl acrylates, of ethyl acrylate (EA or EtA).

According to a specific embodiment, the block A and/or the block B' or B comprises from 0.1 to 10% by weight, preferably from 0.1 to 5% by weight, of hydrophilic comonomer, in particular methacrylic acid or one of its salts, with respect to the total weight of the block A or of the block B or B' comprising the said hydrophilic comonomer.

Thus, during stage Ia), it is possible to use a mixture of monomers comprising at least 90% by weight, preferably at least 95% by weight, of styrene and up to 10% by weight, preferably up to 5% by weight, of methacrylic acid.

During stage Ib), it is possible to use a mixture of monomers comprising at least 90% by weight, preferably at least 95% by weight, of $C_1$-$C_4$ alkyl acrylate, such as ethyl acrylate, and up to 10% by weight, preferably up to 5% by weight, of methacrylic acid or one of its salts.

A few characteristics of the process for the preparation of the copolymers of the invention are explained in detail below.

Stage I)

The copolymers according to the invention can be obtained by any known method, whether by controlled or uncontrolled radical polymerization, by ring opening polymerization (in particular anionic or cationic), by anionic or cationic polymerization, or by chemical modification of a polymer.

Preferably, for the polymerization stage I), use is made of "living" or "controlled" radical polymerization methods and particularly preferably of controlled or living radical polymerization methods employing a transfer agent comprising a transfer group of formula —S—CS—, known in particular under the names of RAFT or MADIX.

Reference may in particular be made, as examples of "living" or "controlled" polymerization processes, to:
- the processes of Applications WO 98/58974, WO 00/75207 and WO 01/42312, which employ a radical polymerization controlled by control agents of xanthate type,
- the radical polymerization process controlled by control agents of dithioester or trithiocarbonate type of Application WO 98/01478,
- the radical polymerization process controlled by control agents of dithiocarbamate type of Application WO 99/31144,
- the radical polymerization process controlled by control agents of dithiocarbazate type of Application WO 02/26836,
- the radical polymerization process controlled by control agents of dithiophosphoric ester type of Application WO 02/10223,
- the process of Application WO 99/03894, which employs a polymerization in the presence of nitroxide precursors, or processes employing other nitroxides or nitroxide/alkoxyamine complexes,
- the process of Application WO 96/30421, which uses an atom transfer radical polymerization (ATRP),
- the radical polymerization process controlled by control agents of iniferter type according to the teaching of Otu et al., Makromol. Chem. Rapid. Commun., 3, 127 (1982),
- the radical polymerization process controlled by iodine degenerative transfer according to the teaching of Tatemoto et al., Jap. 50, 127, 991 (1975), Daikin Kogyo Co Ltd Japan, and Matyjaszewski et al., Macromolecules, 28, 2093 (1995),
- the radical polymerization process controlled by tetraphenylethane derivatives disclosed by D. Braun et al. in Macromol. Symp., 111, 63 (1996), or also
- the radical polymerization process controlled by organocobalt complexes described by Wayland et al. in J. Am. Chem. Soc., 116, 7973 (1994),
- the radical polymerization process controlled by diphenylethylene (WO 00/39169 or WO 00/37507).

The polymerizations can be carried out in emulsion in water ("latex" process). These processes can employ emulsifying agents, generally surfactants. Without wishing to be committed to any one theory, it is believed that the emulsion preparation processes result in the formation of nodules of blocks A, which can influence the physicochemical properties of the copolymer.

The polymerizations can be carried out in the presence of free radical initiators known to a person skilled in the art. Use may be made, for example, of sodium persulphate. It is typically possible to employ amounts of initiators of 5 to 50% by number, with respect to the amount of transfer agent.

Stage II)

During stage II), the respective amounts of the various units in the block B are controlled by the degree of hydrolysis. The composition of the block A may remain unchanged during hydrolysis if the block A does not comprise hydrolysable units. However, it is not out of the question for the block A to be slightly modified during the hydrolysis stage.

Preferably, the hydrolysis stage II) is carried out by addition of a strong base, such as sodium hydroxide or potassium hydroxide. Typically, a proportion by number of base, with respect to the amount of hydrolysable monomer used during stage Ib), is added which corresponds approximately to the targeted degree of hydrolysis, with optionally an excess of a few %. For example, an amount of sodium hydroxide of 75% by number of the amount of hydrolysable ethyl acrylate employed during stage Ib) is introduced. An operation of homogeneous hydrolysis is preferably carried out by gradually adding the sodium hydroxide to the copolymer.

The hydrolysis stage can result in particular in the deactivation and/or the severing of certain transfer groups or other groups attached to the macromolecular chains. Stage II) can thus generate by-products which it is desirable to remove or generate groups on the macromolecular chains which it is desirable to chemically modify. Such operations can be carried out during a stage III).

Stage III)

Stage III) is a stage of deactivation of transfer groups carried by macromolecular chains and/or of purification of the (block A)-(block B) diblock copolymer and/or of destruction of hydrolysis and/or deactivation by-products.

During the optional stage III), the block copolymers obtained or the hydrolysis by-products can be subjected to a reaction for purification from or destruction of certain entities, for example by processes of hydrolysis, oxidation, reduction, pyrolysis, ozonolysis or substitution type. A stage of oxidation with aqueous hydrogen peroxide solution is particularly appropriate for treating sulphur-comprising entities. It is mentioned that some of these reactions or operations can take place entirely or in part during stage II). In this case, for these reactions or operations, the two stages are simultaneous.

The average molecular weights of the (block A)-(block B') diblock copolymer before hydrolysis or of each of the blocks typically depend on the relative amounts of the monomers and transfer agent employed during stage I). Of course, the average molecular weights of the (block A)-(block B) diblock copolymer after hydrolysis or of each of the blocks depend on these same relative amounts and also on the degree of hydrolysis, for example depend on the amount of reactant introduced, generally a base, for this hydrolysis.

For the sake of simplicity, it is common to express the average molecular weights of the blocks as "theoretical" or "targeted" average molecular weights, taking into consideration a complete and perfectly controlled polymerization. In this case, one macromolecular chain is formed per transfer agent; in order to obtain the molecular weight, it is sufficient to multiply the average molar mass of the units of a block by the number of units per block (amount by number of monomer by amount by number of transfer agent). The differences caused by small amounts of comonomers, such as methacrylic acid, can be ignored in these calculations. The theoretical or targeted average molecular weights of the block B are expressed taking into consideration complete hydrolysis (the weights are expressed with the fiction of a degree of hydrolysis of 1).

The theoretical average molecular weight $M_{block}$ of a block is typically calculated according to the following formula:

$$M_{block} = \sum_i M_i * \frac{n_i}{n_{precursor}},$$

where $M_i$ is the molar mass of a monomer i, $n_i$ is the number of moles of the monomer i and $n_{precursor}$ is the number of moles of functional groups to which the macromolecular chain of the block will be bonded. The functional groups can originate from a transfer agent (or a transfer group) or an initiator, a preceding block, and the like. If a preceding block is concerned, the number of moles can be regarded as the number of moles of a compound to which the macromolecular chain of the said preceding block has been bonded, for example a transfer agent (or a transfer group) or an initiator. In practice, the theoretical average molecular weights are calculated from the number of moles of monomers introduced and from the number of moles of precursor introduced.

The theoretical or targeted average molecular weight of a block copolymer is considered to be the addition of the average molecular weights of each of the blocks, taking into consideration complete hydrolysis (the weights are expressed with the fiction of a degree of hydrolysis of 1), if such a hydrolysis has been carried out.

The targeted or theoretical total weight of a block is defined as the weight of the macromolecular chain, taking into consideration a complete and perfectly controlled polymerization. In order to obtain the total weight, it is sufficient to multiply the molar mass of a unit of a block by the number per block of this unit and to add the weights thus obtained for each type of unit in the block. The differences caused by small amounts of comonomers, such as methacrylic acid, can be ignored in these calculations. The theoretical or targeted total weights of the block B are expressed taking into consideration the effects of a partial hydrolysis (the fiction of a degree of hydrolysis of 1 is not used for this descriptor), if such a hydrolysis has been carried out.

Thus:
- the theoretical or targeted total weight of the block A is $M_A n_A$; the theoretical or targeted average molecular weight of the block A is: $M_A n_A / n_T$,
- the theoretical or targeted total weight of the block B' is $M_B n_B$; the theoretical or targeted average molecular weight of the block B' is: $M_B n_B / n_T$,
- the theoretical or targeted total weight of the block B is $T M_{AA} n_B + (1-T) M_B n_B$; the theoretical or targeted average molecular weight of the block B is: $M_{AA} n_B / n_T$ (as T=1 for the theoretical or targeted average molecular weight),
- the theoretical or targeted total weight of the block copolymer is $$M_A n_A + T M_{AA} n_B + (1-T) M_B n_B;$$

the theoretical or targeted average molecular weight of the (block A)-(block B) block copolymer is $n_A/n_T M_A + M_{AA} n_B / n_T$, where:
- $M_A$ is the molar mass of styrene or of the mixture of monomers comprising styrene employed in stage Ia),
- $M_{AA}$ is the molar mass of acrylic acid,
- $M_B$ is the molar mass of the $C_1$-$C_4$ alkyl acrylate or of the mixture of monomers comprising the $C_1$-$C_4$ alkyl acrylate employed in stage Ib).

The following correspondences are given as reference points:
- $n_A/n_T$=5 corresponds to a theoretical average molecular weight of the block A of approximately 500 g/mol,
- $n_A/n_T$=5000 corresponds to a theoretical average molecular weight of the block A of approximately 500 000 g/mol,
- $n_B/n_T$=5 corresponds to a theoretical average molecular weight of the block B' of approximately 500 g/mol,
- $n_B/n_T$=5000 corresponds to a theoretical average molecular weight of the block B' of approximately 500 000 g/mol,
- $n_A/n_T M_A + M_{AA} n_B/n_T$=13 000 g/mol (resp. 2000, resp. 8000, resp. 20 000, resp. 50 000) corresponds to a theoretical average molecular weight of the (block A)-(block B) diblock of approximately 13 000 g/mol (resp. 2000, resp. 8000, resp. 20 000, resp. 50 000), taking into consideration a complete hydrolysis and for the case where the $C_1$-$C_4$ alkyl acrylate is ethyl acrylate.

The ratios by weight between the blocks are defined as the ratios between the theoretical or targeted total weights (the fiction of a degree of hydrolysis of 1 is not used for this descriptor).

Thus:
$M_A n_A \leq T M_{AA} n_B + (1-T) M_B n_B$ indicates that the (block B)/(block A) ratio by weight $\geq 1$. This is a characteristic of the copolymer employed according to the invention, $M_A n_A/[M_A n_A + TM_{AA} n_B + (1-T)M_B n_B]$ indicates the amount by weight of block A in the (block A)-(block B) diblock copolymer, that is to say the proportion of block A, $[TM_{AA} n_B + (1-T)M_B n_B]/[M_A n_A + TM_{AA} n_B + (1-T)M_B n_B]$ indicates the amount by weight of block B in the (block A)-(block B) diblock copolymer, that is to say the proportion of block B.

It is mentioned that it would not be departing from the scope of the invention to employ and to adapt other processes of preparation resulting in substantially identical diblock copolymers. In particular, it is possible to envisage employing transfer agents comprising several transfer groups (for example trithiocarbonates Z—S—CS—S—Z) which result in telechelic copolymers of R-[(block B')-(block A)]$_w$ type (for example (block A)-(block B')-R-(block B')-(block A) and then to sever ("cleave") the telechelic copolymers in order to obtain (block A)-(block B') diblock copolymers. The severing can occur during the hydrolysis, in which case (block A)-(block B) diblock copolymers are obtained directly. In such cases, a person skilled in the art will adjust the operating conditions in order to target average molecular weights equivalent to those indicated, for example by multiplying the amounts of monomers introduced by the number of transfer groups included in the transfer agent.

Preferably, the linear (block A)-(block B) diblock copolymers of the type (1) in which the proportion by weight of the block B with respect to the copolymer $[TM_{AA} n_B + (1-T)M_B n_B]/[M_A n_A + TM_{AA} n_B + (1-T)M_B n_B]$ is between 50 and 85%, preferably between 50 and 75%, and generally have a theoretical average molar mass $(n_A M_T M_A + M_{AA} n_B/n_T)$ of less than or equal to 13 000 g/mol and in particular of between 8000 and 13 000 g/mol.

Preferably, the linear (block A)-(block B) diblock copolymers of the type (2) in which the proportion by weight of the block B with respect to the copolymer $[TM_{AA} n_B + (1-T)M_B n_B]/[M_A n_A + TM_{AA} n_B + (1-T)M_B n_B]$ which is greater than or equal to 85% (BOL 44 and 55 and 64) and generally have a theoretical average molecular weight $(n_A/n_T M_A + M_{AA} n_B/n_T)$ of greater than or equal to 13 000 g/mol.

Among these copolymers of type (2),
those characteristic of the type (2a), where the proportion by weight of the block B with respect to the copolymer is greater than or equal to 87%, in particular greater than or equal to 87%, and less than 94%, generally have a theoretical average molecular weight of between 13 000 and 20 000 g/mol,
those characteristic of the type (2b) where the proportion by weight of the block B with respect to the copolymer is greater than or equal to 94%, in particular ranging from 94% to 97%, generally have a theoretical average molecular weight of greater than or equal to 20 000 g/mol and preferably of between 20 000 and 50 000 g/mol.

The amount (as active material) of amphiphilic copolymer based on polystyrene can range in particular from 0.5 to 1.5% by weight, with respect to the total weight of the composition.

4) Polymers Derived from Polyether

The preferred polymers derived from polyether of the invention are water-soluble polyurethanes, such as, for example:
the PEG-150 copolymer carrying stearyl ends via urethane bonds, sold under the name Aculyn 46 by Röhm & Haas,
the PEG-150 copolymer carrying decyl ends via urethane bonds, sold under the name Aculyn 44 by Röhm & Haas,
the PEG-136 copolymer carrying stearyl ends via urethane bonds, sold under the name Rheolate FX 1100 by Elementis,
the PEG-50 copolymer carrying stearyl ends via urethane bonds, sold under the name Borchigel LW 44 by Borchers France.

The polymers derived from polyether can also carry fatty chains without urethane bonds, such as, for example, the product Pure Thix HH sold by Süd-Chemie.

5) Polymers of Natural Origin

Mention may be made, as polymers of natural origin, of:
cellulose derivatives modified by fatty chains comprising from 6 to 30 carbon atoms, such as:
  cetyl hydroxyethylcelluloses, such as Natrosol CS Plus 330, 430 and Polysurf 67 CS, which are sold by Hercules,
  hydroxypropylmethylcelluloses modified by stearyloxyhydroxypropyl chains to a molar degree of between 0.3 and 0.6%, sold under the names Sangelose 60L (molar mass of the order of 500 000 g/mol) and Sangelose 90 L (molar mass of the order of 900 000 g/mol) by Daido,
  hydroxyethylcellulose quaternized by substituted lauryldimethylammonium epoxide, sold under the name Quadrisoft LM 200 by Amerchol,
  quaternized hydroxyethylcellulose modified by lauryl or stearyl chains, sold under the name Crodacel QM (C12), QL (C12) and QS (C18) by Croda,
  hydroxyethylcelluloses quaternized by trimethylammonium groups and substituted by dimethyldodecylammonium chains, sold under the name Soft Cat SL 5, SL 30, SL 60 and SL 100 by Amerchol,
guar derivatives modified by fatty chains comprising from 6 to 30 carbon atoms, such as the hydroxypropyl guar modified by behenyl chains sold under the name of Esaflor HM 22 by Lamberti,
starch derivatives modified by fatty chains comprising from 6 to 30 carbon atoms, such as the maize starch esterified by octenylsuccinic anhydride in the sodium salt form sold under the name N-Creamer 46 by National Starch,
acacia gum derivatives modified by fatty chains comprising from 6 to 30 carbon atoms, such as the acacia gum modified by controlled esterification sold under the name Ticamulsion A-2010 by Tic Gums.

These polymers exhibit the advantage of being relatively insensitive to pH variations for values of between 4 and 8, which are the normal values of cosmetic compositions.

Use is in particular made of cellulose derivatives in a content (as active material) of polymer ranging from 0.3 to 2% by weight, better still from 0.5 to 2% by weight, with respect to the total weight of the composition.

Emulsifiers

In order to facilitate the emulsification of the oily phase, the composition according to the invention can comprise one or more emulsifiers (separate from the amphiphilic polymer), also known as "coemulsifiers".

The amount (as active material) of emulsifier(s) can range, for example, from 0.001% to 5% by weight, preferably from 0.005% to 2% by weight and better still from 0.01% to 1% by weight, with respect to the total weight of the composition.

The emulsifier is preferably used at a level of less than 20% by weight, with respect to the weight of amphiphilic polymer.

The emulsifier can be chosen from alkylpolyglucosides, polyoxyethylene (POE) alkyl esters or ethers, glycerol alkyl esters or ethers, oxyethylenated or nonoxyethylenated sorbitan alkyl esters or ethers, dimethicone copolyols, gemini surfactants or mono- or disodium acylglutamates.

Mention may in particular be made of:
glycerol esters, such as glycerol mono- or polyalkyl esters or ethers, such as described in the documents EP 1 010 416 and EP 1 010 414, glyceryl monoisostearate, such as the product sold under the name Peceol Isostéarique by Gattefossé, the polyglycerolated (4 mol) isostearate sold under the name Isolan GI34 by Goldschmidt, the polyglycerolated (3 mol) diisostearate sold under the name Lameform TGI by Cognis and the polyglycerolated (2 mol) distearate sold under the name Emalex PGSA by Nihon Emulsion.
polyethylene glycol esters and ethers, such as polyethylene glycol alkyl esters and ethers, such as described in the documents EP 1 120 101 and EP 1 016 453, Oleth-50, sold under the name Emalex 550 by Nihon Emulsion, Oleth-20, sold under the name Brij 98 by Uniqema, Ceteth-2 and Ceteth-10, sold under the names Brij 52 and 56 by Uniqema, Laureth-23, sold under the name Brij 35 by Uniqema, PEG-8 stearate, sold under the name Myrj 45 by Uniqema, PEG-8 isostearate, such as the product sold under the name Prisorine 3644 by Uniqema, and PEG-20 stearate and PEG-40 stearate, sold under the names Myrj 49 and Myrj 52 by Uniqema.

Mention may also be made of the following compounds, sold by Uniqema:

| Trade name | INCI name |
| --- | --- |
| Brij 35 | Laureth-23 |
| Brij 30 | Laureth-4 |
| Brij 96 | Oleth-10 |
| Brij 56 | Ceteth-10 |
| Brij 98 | Oleth-20 |
| Brij 76 | Steareth-10 |
| Brij 72 | Steareth-2 |
| Brij 52 | Ceteth-2 |
| Brij 78 | Steareth-20. | sorbitan esters or ethers, such as oxyethylenated or nonoxyethylenated sorbitan mono- or polyalkyl esters or ethers, such as described in the document EP 1 010 415, or also the following products, sold by Uniqema:

| Trade name | INCI name |
| --- | --- |
| Tween 21 | Polysorbate 21 |
| Tween 40 | Polysorbate 40 |
| Tween 80 | Polysorbate 80 |
| Tween 60V | Polysorbate 60 |
| Tween 61V | Polysorbate 61. |

Mention is also made of sorbitan isostearate, such as the product sold under the name Arlacel 987 by Uniqema, glyceryl sorbitan isostearate, such as the product sold under the name Arlacel 986 by Uniqema, sorbitan sesquioleate, such as the product sold under the name Arlacel 83V by Uniqema, sorbitan laurate, sorbitan monopalmitate, sorbitan oleate, sorbitan trioleate, sorbitan monostearate and sorbitan tristearate, such as the products sold under the names Span 20, Span 40, Span 80V, Span 85V, Span 60 and Span 65V by Uniqema.

Sugar mono- or polyalkyl esters or ethers, such as the mono- or polyalkyl esters or ethers of sugars as described in the U.S. Pat. No. 6,689,371. Mention may be made, for example, of methyl glucose isostearate, such as Isolan-IS from Degussa Goldschmidt, or also sucrose distearate, such as Crodesta F50, sold by Croda, and sucrose stearate, such as Ryoto Sugar Ester S1570, sold by Mitsubishi Kagaku Foods.

Alkoxylated alkenyl succinates, for example as described in the document EP 1 025 898.

Fatty alcohols, such as fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol and their mixtures.

Silicone derivatives, such as dimethicone copolyols, for example the mixture of cyclomethicone and of dimethicone copolyol sold under the name "DC 5225 C" by Dow Corning, and alkyl dimethicone copolyols, such as lauryl methicone copolyol, sold under the name "Dow Corning 5200 Formulation Aid" by Dow Corning, and cetyl dimethicone copolyol, sold under the name "Abil EM 90" by Goldschmidt, or the polyglyceryl-4 isostearate/cetyl dimethicone copolyol/hexyl laurate mixture sold under the name "Abil WE 90" by Goldschmidt.

Alkoxylated alkenyl succinates, such as, for example, those which are described in the document EP 1 025 898.

Alkyl phosphoric esters, such as, for example, those which are described in the document EP 1 013 338.

Alkyl ether citrates, such as, for example, those which are described in the document EP 1 020 219.

Lipoamino acids and their salts, such as mono- and disodium acylglutamates, such as, for example, monosodium stearoyl glutamate (Amisoft HS-11PF) and disodium stearoyl glutamate (Amisoft HS-21P), sold by Ajinomoto.

Alkyl phosphates and their salts, such as the alkali metal salts of dicetyl and dimyristyl phosphate, or also potassium cetyl phosphate, such as Amphisol K, sold by DSM Nutritional Products.

Cholesterol derivatives, such as the alkali metal salts of cholesterol sulphate or the alkali metal salts of cholesterol phosphate.

Ammonium salts of phosphatidic acid.

Phospholipids.

Alkylsulphonic derivatives, such as described in the patent document EP 1 120 101.

According to a preferred form of the invention, the coemulsifier is chosen from glyceryl esters (glyceryl isostearate), sorbitan esters (Polysorbate 60) and polyethylene glycol esters (PEG 8 isostearate).

Aqueous Phase

The aqueous phase of the composition according to the invention comprises water and optionally one or more compounds which are miscible with water or at least partially miscible with water, such as polyols or lower $C_2$ to $C_8$ monoalcohols, such as ethanol and isopropanol. The term "ambient temperature" should be understood as meaning a temperature of approximately 25° C. at standard atmospheric pressure (760 mmHg).

The term "polyol" should be understood as meaning any organic molecule comprising at least two free hydroxyl groups. Mention may be made, as polyols, for example, of glycols, such as butylene glycol, propylene glycol, isoprene glycol, glycerol and polyethylene glycols, such as PEG-8, sorbitol or sugars, such as glucose.

The aqueous phase can also comprise any normal water-soluble or water-dispersible additive as indicated below.

The aqueous phase can represent from 60 to 98% by weight, preferably from 65 to 95% by weight, better still from 70 to 90% by weight and even better still from 70 to 85% by weight, with respect to the total weight of the composition.

The water-miscible compound or compounds, such as polyols and lower alcohols, can be present in an amount ranging from 0 to 30% of the total weight of the composition, in particular from 0.1 to 30% and better still in an amount ranging from 1 to 20%.

Oily Phase

The nature of the oily phase of the emulsion according to the invention is not critical. The oily phase is a fatty phase comprising at least one fatty substance chosen from fatty substances which are liquid at ambient temperature (20-25° C.) or volatile or non-volatile oils of vegetable, mineral or synthetic origin, and their mixtures. These oils are physiologically acceptable.

The oily phase can also comprise any normal fat-soluble or fat-dispersible additive as indicated below.

It can in particular comprise other fatty substances, such as waxes, pasty compounds, fatty alcohols or fatty acids. The oily phase comprises at least one oil, more particularly at least one cosmetic oil. The term "oil" is understood to mean a fatty substance which is liquid at ambient temperature (25° C.).

Mention may be made, as oils which can be used in the composition of the invention, for example, of:

hydrocarbon oils of animal origin, such as perhydrosqualene;

hydrocarbon oils of vegetable origin, such as liquid triglycerides of fatty acids comprising from 4 to 10 carbon atoms, such as triglycerides of heptanoic acid or octanoic acid, or also, for example, sunflower, maize, soybean, cucumber, grape seed, sesame, hazelnut, apricot, macadamia, arara, coriander, castor or avocado oils, triglycerides of caprylic/capric acids, such as those sold by Stéarineries Dubois or those sold under the names Miglyol 810, 812 and 818 by Dynamit Nobel, jojoba oil or shea butter oil;

synthetic esters and ethers, in particular of fatty acids, such as oils of formulae $R^1COOR^2$ and $R^1OR^2$ in which $R^1$ represents the residue of a fatty acid or of a fatty alcohol comprising from 8 to 29 carbon atoms and $R^2$ represents a branched or unbranched hydrocarbon chain comprising from 3 to 30 carbon atoms, such as, for example, purcellin oil, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate;

linear or branched hydrocarbons of mineral or synthetic origin, such as volatile or non-volatile liquid paraffins and their derivatives, liquid petrolatum, polydecenes, isohexadecane, isododecane or hydrogenated polyisobutene, such as Parleam® oil;

fluorinated oils which partially comprise hydrocarbon and/or silicone, such as those described in the document JP-A-2-295912;

silicone oils, such as volatile or non-volatile polymethylsiloxanes (PDMSs) comprising a linear or cyclic silicone chain which are liquid or pasty at ambient temperature, in particular volatile silicone oils, especially cyclopolydimethylsiloxanes (cyclomethicones), such as cyclohexadimethylsiloxane and cyclopentadimethylsiloxane; polydimethylsiloxanes comprising pendant alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes, (2-phenylethyl)trimethylsiloxysilicates and polymethylphenylsiloxanes;

their mixtures.

According to a preferred embodiment, the composition of the invention comprises at least one oil chosen from silicone oils, linear or branched hydrocarbons, synthetic ethers and esters, and their mixtures, in particular chosen from volatile silicone oils and branched hydrocarbons, such as Parleam® oil, and their mixtures.

The amount of oily phase in the composition of the invention is less than 35% by weight of the total weight of the composition, preferably less than or equal to 33% by weight and better still less than or equal to 32% by weight. The amount of oily phase can range, for example, from 2 to 35% by weight, preferably from 5 to 33% by weight, better still from 10 to 33% by weight and even better still from 15 to 30% by weight, with respect to the total weight of the composition.

As indicated above, this amount of oily phase does not include the amount of emulsifier.

According to one embodiment, the composition according to the invention comprises less than 35% by weight of oils, with respect to the total weight of the composition, preferably less than 33% by weight and better still less than 32% by weight.

Additives

In a known way, the composition for topical application of the invention can also comprise one or more adjuvants normal in the cosmetic or dermatological field. Mention may be made, as adjuvants, of gelling agents, active principles, preservatives, antioxidants, fragrances, solvents, salts, fillers, sunscreens (=UV screening agents), colouring materials, basic agents (triethanolamine, diethanolamine, sodium hydroxide) or acidic agents (citric acid), and also lipid vesicles or any other type of vector (nanocapsules, microcapsules, and the like), and their mixtures. These adjuvants are used in the proportions usual in the cosmetic field, for example from 0.01 to 30% of the total weight of the composition, and they are, depending on their nature, introduced into the aqueous phase of the composition or into the oily phase, or also into vesicles or any other type of vector. These adjuvants and their concentrations must be such that they do not modify the property desired for the emulsion of the invention.

Depending on the viscosity desired for the composition according to the invention, it is possible to incorporate therein one or more hydrophilic gelling agents. Mention may be made, as hydrophilic gelling agents, for example, of modified or unmodified carboxyvinyl polymers, such as the products sold under the Carbopol name (INCI name: carbomer) by Noveon; polyacrylamides; optionally crosslinked and/or neutralized polymers and copolymers of 2-acrylamido-2-methylpropanesulphonic acid, such as the poly(2-acrylamido-2-methylpropanesulphonic acid) sold by Clariant under the name "Hostacerin AMPS" (INCI name: ammonium polyacryldimethyltauramide); crosslinked anionic copolymers of acrylamide and of AMPS which are provided in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by SEPPIC; polysaccharide biopolymers, such as xanthan gum, guar gum, alginates or modified or unmodified celluloses; and their mixtures. When they are present, these gelling agents have to be introduced in an amount such that they do not modify the properties of the composition according to the invention. Mention may in particular be made, as lipophilic gelling agents, of modified clays, such as modified magnesium silicate (bentone gel VS38 from Rheox) or hectorite modified with distearyldimethylammonium chloride (INCI name: Disteardimonium hectorite), sold under the name "bentone 38 CE" by Rheox.

The gelling agent can be present in a content as active material ranging from 0.05% to 10% by weight and preferably from 0.1% to 5% by weight, with respect to the total weight of the composition.

Mention may be made, as fillers which can be used in the composition of the invention, for example, of pigments, such as titanium, zinc or iron oxides and organic pigments; kaolin; silica; talc; boron nitride; spherical organic powders; fibres; and their mixtures. Mention may be made, as spherical organic powders, for example, of polyamide powders and in particular Nylon®, such as Nylon-1 or Polyamide 12, powders sold under the Orgasol names by Atochem; polyethylene powders; Teflon®; microspheres based on acrylic copolymers, such as those made of ethylene glycol dimethacrylate/lauryl methacrylate copolymer sold by Dow Corning under the name Polytrap; expanded powders, such as hollow microspheres and in particular the microspheres sold under the name Expancel by Kemanord Plast or under the name Micropearl F 80 ED by Matsumoto; silicone resin microbeads, such as those sold under the name Tospearl by Toshiba Silicone; polymethyl methacrylate microspheres, sold under the name Microsphere M-100 by Matsumoto or under the name Covabead LH85 by Wackherr; ethylene/acrylate copolymer powders, such as those sold under the name Flobeads by Sumitomo Seika Chemicals; or powders formed from natural organic materials, such as starch powders, in particular powders formed from crosslinked or noncrosslinked maize, wheat or rice starches, such as the powders formed from starch crosslinked with octenyl succinic anhydride sold under the name Dry-Flo by National Starch. Mention may be made, as fibres, for example, of polyamide fibres, such as in particular fibres formed from Nylon 6 (or Polyamide 6) (INCI name: Nylon 6) or from Nylon 6,6 (or Polyamide 66) (INCI name: Nylon 66) or such as fibres formed from poly(p-phenylene terephthalamide); and their mixtures. These fillers can be present in amounts ranging from 0 to 20% by weight and preferably from 0.5 to 10% by weight, with respect to the total weight of the composition.

Mention may be made, as active principles which can be used in the composition of the invention, for example, of moisturizing agents, such as protein hydrolysates; sodium hyaluronate; polyols, such as glycerol, glycols, such as polyethylene glycols, and sugar derivatives; antiinflammatories; procyanidol oligomers; vitamins, such as vitamin A (retinol), vitamin E (tocopherol), vitamin K, vitamin C (ascorbic acid), vitamin B5 (panthenol), vitamin B3 or PP (niacinamide), the derivatives of these vitamins (in particular esters) and their mixtures; keratolytic and/or desquamating agents, such as salicylic acid and its derivatives, α-hydroxy acids, such as lactic acid and glycolic acid, and their derivatives, and ascorbic acid and its derivatives; urea; caffeine; depigmenting agents, such as kojic acid, hydroquinone and caffeic acid; salicylic acid and its derivatives; retinoids, such as carotenoids and vitamin A derivatives; hydrocortisone; melatonin; algal, fungal, plant, yeast or bacterial extracts; steroids; antibacterial active principles, such as 2,4,4'-trichloro-2'-hydroxydiphenyl ether (or triclosan), 3,4,4'-trichlorocarbanilide (or triclocarban) and the acids indicated above and in particular salicylic acid and its derivatives; enzymes; flavonoids; tightening agents, such as synthetic polymers, plant proteins, polysaccharides of plant origin in or not in the form of microgels, starches, wax dispersions, mixed silicates and colloidal particles of inorganic fillers; ceramides; antiinflammatory agents; soothing agents; mattifying agents; agents for combating hair loss and/or for regrowth of the hair; antiwrinkle agents; essential oils; and their mixtures; and any active principle appropriate for the final objective of the composition.

The UV screening agents can be organic or inorganic (or physical UV screening agents). They can be present in an amount as active material ranging from 0.01 to 20% by weight of active material, preferably from 0.1 to 15% by weight and better still from 0.2 to 10% by weight, with respect to the total weight of the composition.

Mention may be made, as examples of organic screening agents active in the UV-A and/or UV-B regions which can be added to the composition of the invention, for example, of dibenzoylmethane derivatives, anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives, especially those mentioned in U.S. Pat. No. 5,624,663; benzimidazole derivatives; imidazolines; bisbenzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. Nos. 5,237,071, 5,166,355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981; merocyanin derivatives such as those described in patent applications WO 04/006 878, WO 05/058 269 and WO 06/032 741; and mixtures thereof.

As examples of organic UV-screening agents, mention may be made of those denoted hereinbelow under their INCI name:

dibenzoylmethane Derivatives:
2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4,4'-dimethoxydibenzoylmethane 4-tert-butyl-4'-methoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane.

Among the dibenzoylmethane derivatives mentioned above, 4-isopropyldibenzoylmethane will be used in particular, which is sold under the name Eusolex 8020 by the company Merck, and corresponds to the following formula:

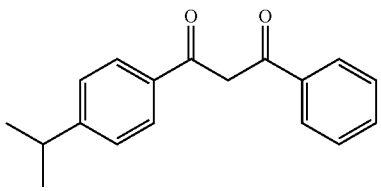 [SMILES: CC(C)c1ccc(C(=O)CC(=O)c2ccccc2)cc1]

It is most particularly preferred to use 4-(tert-butyl)-4'-methoxydibenzoylmethane or Butyl Methoxy Dibenzoylmethane, sold under the trade name Parsol 1789 by the company DSM Nutritional Products; this screening agent corresponds to the following formula:

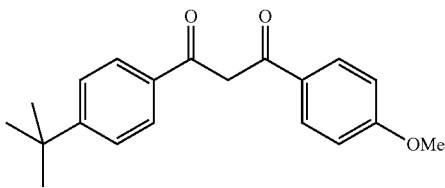 [SMILES: COc1ccc(C(=O)CC(=O)c2ccc(C(C)(C)C)cc2)cc1]

para-Aminobenzoic Acid Derivatives:
  PABA,
  Ethyl PABA,
  Ethyl dihydroxypropyl PABA,
  Ethylhexyl dimethyl PABA sold in particular under the name Escalol 507 by ISP, Glyceryl PABA,
  PEG-25 PABA sold under the name Uvinul P25 by BASF.
Salicylic Derivatives:
  Homosalate sold under the name Eusolex HMS by Rona/EM Industries,
  Ethylhexyl salicylate sold under the name Neo Heliopan OS by Haarmann and Reimer,
  Dipropylene glycol salicylate sold under the name Dipsal by Scher,
  TEA salicylate sold under the name Neo Heliopan TS by Haarmann and Reimer.
Cinnamic Derivatives:
  Ethylhexyl methoxycinnamate sold in particular under the trade name Parsol MCX by Hoffmann LaRoche,
  Isopropyl methoxycinnamate,
  Isoamyl methoxycinnamate sold under the trade name Neo Heliopan E 1000 by Haarmann and Reimer,
  Cinoxate,
  DEA methoxycinnamate,
  Diisopropyl methylcinnamate,
  Glyceryl ethylhexanoate dimethoxycinnamate.
β,β-Diphenylacrylate Derivatives:
  Octocrylene sold in particular under the trade name Uvinul N539 by BASF,
  Etocrylene sold under the trade name Uvinul N35 by BASF.

Benzophenone Derivatives:
  Benzophenone-1 sold under the trade name Uvinul 400 by BASF,
  Benzophenone-2 sold under the trade name Uvinul D50 by BASF,
  Benzophenone-3 or Oxybenzone sold under the trade name Uvinul M40 by BASF,
  Benzophenone-4 sold under the trade name Uvinul MS40 by BASF,
  Benzophenone-5,
  Benzophenone-6 sold under the trade name Helisorb 11 by Norquay,
  Benzophenone-8 sold under the trade name Spectra-Sorb UV-24 by American Cyanamid,
  Benzophenone-9 sold under the trade name Uvinul DS-49 by BASF,
  Benzophenone-12
  n-hexyl 2-(4-diethylamino-2-hydroxybenzoyl)benzoate sold under the trade name Uvinul A+, or in the form of a mixture with octyl methoxycinnamate under the trade name Uvinul A+B by BASF.
Benzylidenecamphor Derivatives:
  3-Benzylidenecamphor manufactured under the name Mexoryl SD by Chimex,
  4-Methylbenzylidenecamphor sold under the name Eusolex 6300 by Merck,
  Benzylidenecamphorsulfonic acid manufactured under the name Mexoryl SL by Chimex, Camphor benzalkonium methosulfate manufactured under the name Mexoryl SO by Chimex,
  Terephthalylidenedicamphorsulfonic acid manufactured under the name Mexoryl SX by Chimex,
  Polyacrylamidomethylbenzylidenecamphor manufactured under the name Mexoryl SW by Chimex.
Phenylbenzimidazole Derivatives:
  Phenylbenzimidazolesulfonic acid sold in particular under the trade name Eusolex 232 by Merck,
  Disodium phenyl dibenzimidazole tetrasulfonate sold under the trade name Neo Heliopan AP by Haarmann and Reimer.
Phenylbenzotriazole Derivatives:
  Drometrizole trisiloxane sold under the name Silatrizole by Rhodia Chimie, Methylenebis(benzotriazolyl)tetramethylbutylphenol sold in solid form under the trade name MIXXIM BB/100 by Fairmount Chemical, or in micronized form as an aqueous dispersion under the name Tinosorb M by Ciba Specialty Chemicals.
Triazine Derivatives:
  Bis(ethylhexyloxyphenol)methoxyphenyltriazine sold under the trade name Tinosorb S by Ciba Geigy, Ethylhexyltriazone sold in particular under the trade name Uvinul T150 by BASF,
  Diethylhexylbutamidotriazone sold under the trade name Uvasorb HEB by Sigma 3V, 2,4,6-tris(diisobutyl 4'-aminobenzalmalonate)-s-triazine,
  2,4,6-tris(dineopentyl 4'-aminobenzalmalonate)-s-triazine
  2,4-bis(dineopentyl 4'-aminobenzalmalonate)-6-(n-butyl 4'-aminobenzoate)-s-triazine,
  the symmetrical triazine screening agents described in U.S. Pat. No. 6,225,467, patent application WO 2004/085 412 (see compounds 6 and 9) or the document Symmetrical Triazine Derivatives IP.COM Journal, IP.COM INC West Henrietta, N.Y., US (20 Sep. 2004), especially 2,4,6-tris (biphenyl)-1,3,5-triazines (in particular 2,4,6-tris(biphenyl-4-yl-1,3,5-triazine) and 2,4,6-tris(terphenyl)-1,3,5-triazine which is also mentioned in Beiersdorf patent applications WO 06/035 000, WO 06/034 982, WO 06/034 991, WO 06/035 007, WO 2006/034 992 and WO 2006/034 985.

Anthranilic Derivatives:

Menthyl anthranilate sold under the trade name Neo Heliopan MA by Haarmann and Reimer.

Imidazoline Derivatives:

Ethylhexyldimethoxybenzylidenedioxoimidazoline propionate.

Benzalmalonate Derivatives:

Dineopentyl 4'-methoxybenzalmalonate,

Polyorganosiloxane containing benzalmalonate functions, for instance Polysilicone-15, sold under the trade name Parsol SLX by Hoffmann LaRoche 4,4-Diaryl butadiene Derivatives:

1,1-Dicarboxy(2,2'-dimethylpropyl)-4,4-diphenylbutadiene

Benzoxazole Derivatives:

2,4-bis[5-(1-dimethylpropyl)benzoxazol-2-yl(4-phenyl) imino]-6-(2-ethyl hexyl)imino-1,3,5-triazine sold under the name Uvasorb $K_2A$ by Sigma 3V and mixtures thereof.

The total amount of organic UV screening agents in the compositions according to the invention can range, for example, from 0.1 to 20% by weight, with respect to the total weight of the composition, preferably ranging from 0.2 to 15% by weight, with respect to the total weight of the composition.

The mineral screening agents are chosen from coated or uncoated metal oxide pigments in which the mean size of the primary particles is preferentially between 5 nm and 100 nm (preferably between 10 nm and 50 nm), for instance titanium oxide (amorphous or crystallized in rutile and/or anatase form), iron oxide, zinc oxide, zirconium oxide or cerium oxide pigments, which are all UV-photoprotective agents that are well known per se.

The pigments may be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (of titanium or of aluminium), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based radicals being directly attached via a carbon atom to the said silicon atoms.

The term "silicones" also includes the silanes required for their preparation, in particular alkyl silanes.

The silicones used for coating the nanopigments that are suitable for the present invention are preferably chosen from the group containing alkyl silanes, polydialkylsiloxanes and polyalkylhydrogenosiloxanes. Even more preferentially, the silicones are chosen from the group containing octyltrimethylsilane, polydimethylsiloxanes and polymethylhydrogenosiloxanes.

Needless to say, before being treated with silicones, the metal oxide pigments may have been treated with other surface agents, in particular with cerium oxide, alumina, silica, aluminium compounds or silicon compounds, or mixtures thereof.

The coated pigments are more particularly titanium oxides that have been coated:

with silica, such as the product Sunveil from the company Ikeda and the product Eusolex T-AVO from the company Merck, with silica and iron oxide, such as the product Sunveil F from the company Ikeda, with silica and alumina, such as the products Microtitanium Dioxide MT 500 SA and Microtitanium Dioxide MT 100 SA from the company Tayca, Tioveil from the company Tioxide and Mirasun TiW 60 from the company Rhodia, with alumina, such as the products Tipaque TTO-55 (B) and Tipaque TTO-55 (A) from the company Ishihara and UVT 14/4 from the company Kemira, with alumina and aluminium stearate, such as the product Microtitanium Dioxide MT 100 TV, MT 100 TX, MT 100 Z and MT-01 from the company Tayca, and the products Solaveil CT-10 W, Solaveil CT 100 and Solaveil CT 200 from the company Uniqema, with silica, alumina and alginic acid, such as the product MT-100 AQ from the company Tayca, with alumina and aluminium laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, or the product SMT-100 WRS from the company Tayca, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

Other titanium oxide pigments treated with a silicone are preferably $TiO_2$ treated with octyltrimethylsilane and for which the mean size of the elementary particles is between 25 and 40 nm, such as the product sold under the trade name T 805 by the company Degussa Silices, $TiO_2$ treated with a polydimethylsiloxane and for which the mean size of the elementary particles is 21 nm, such as the product sold under the trade name 70250 Cardre UF $TiO_2S13$ by the company Cardre, anatase/rutile $TiO_2$ treated with a polydimethylhydrogenosiloxane and for which the mean size of the elementary particles is 25 nm, such as the product sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackher under the name Transparent titanium oxide PW, by the company Miyoshi Kasei under the name UFTR, by the company Tomen under the name ITS and by the company Tioxide under the name Tioveil AQ.

The uncoated zinc oxide pigments are, for example:
those sold under the name Z-Cote by the company Sunsmart.

The coated zinc oxide pigments are, for example:
those sold under the name Z-Cote HP1 by the company Sunsmart (dimethicone-coated ZnO);
those sold under the name Zinc Oxide CS-5 by the company Toshibi (ZnO coated with polymethylhydrogenosiloxane);
those sold under the name Daitopersion ZN-30 and Daitopersion ZN-50 by the company Daito (dispersions in cyclopolymethylsiloxane/oxyethylenated polydimethylsiloxane, containing 30% or 50% of nanozinc oxides coated with silica and polymethylhydrogenosiloxane);
those sold under the name NFD Ultrafine ZnO by the company Daikin (ZnO coated with perfluoroalkyl phosphate and copolymer based on perfluoroalkylethyl as a dispersion in cyclopentasiloxane);
those sold under the name SPD-Z1 by the company Shin-Etsu (ZnO coated with silicone-grafted acrylic polymer, dispersed in cyclodimethylsiloxane);
those sold under the name Escalol Z100 by the company ISP (alumina-treated ZnO dispersed in an ethylhexyl methoxycinnamate/PVP-hexadecene/methicone copolymer mixture);
those sold under the name Fuji ZnO-SMS-10 by the company Fuji Pigment (ZnO coated with silica and polymethylsilsesquioxane).

The uncoated cerium oxide pigments are sold under the name Colloidal Cerium Oxide by the company Rhone-Poulenc.

The coated iron oxide pigments are sold, for example, by the company BASF under the name Transparent Iron Oxide.

Mention may also be made of mixtures of metal oxides, especially of titanium dioxide and of cerium dioxide, including the silica-coated equal-weight mixture of titanium dioxide and of cerium dioxide, sold by the company Ikeda under the name Sunveil A, and also the alumina, silica and silicone-coated mixture of titanium dioxide and of zinc dioxide, such as the product M 261 sold by the company Kemira, or the alumina, silica and glycerol-coated mixture of titanium dioxide and of zinc dioxide, such as the product M 211 sold by the company Kemira.

The compositions of the invention are advantageously prepared according to a process in which the oily fatty phase, comprising the oils and optionally the other fatty substances, is emulsified in the aqueous phase (into which the amphiphilic polymer has been introduced) with gentle stirring, that is to say with a low degree of shearing.

Stirring is preferably carried out with a magnetic bar or any other stirring system which gives gentle stirring and thus low energy at a temperature which can range from 20° C. to 45° C. The term "gentle stirring" is understood to mean stirring carried out with a degree of shearing of less than 1000 s$^{-1}$.

Another subject-matter of the invention is thus a process for the preparation of the compositions as described above in which the oily fatty phase is introduced into the aqueous phase, comprising the amphiphilic polymer, with gentle shearing.

Thus, the process for emulsification with gentle shearing can be carried out with any other stirring system which gives gentle stirring and thus low energy, such as, for example:
using a paddle or propeller,
in a vessel equipped with a vessel bottom turbine, with a scraping blade or with a contrarotating central mixing paddle and heating/cooling via the jacket of the vessel. Mention may be made, as examples, of the Macef and Maxilab vessels from Olsa or the vessels provided by Pierre Guérin,
using a colloid mill,
using a static emulsifier,
with an in-line turbine, of the IKA or KMF trade mark, for example.

This process is determining for the production of large oil globules in accordance with the invention.

One method of preparation may be the following: the amphiphilic polymer is dissolved in water with stirring at 25° C. for 30 minutes; the solution obtained is macroscopically homogeneous. The emulsion is prepared by slow introduction of the oily phase into the aqueous phase over 20 minutes with stirring using a homogenizer of Rayneri type equipped with a paddle with a stirring rate of 250 rpm.

The compositions according to the invention can be provided, for example, in all the formulation forms for O/W emulsions, for example in the form of serum, milk or cream, and they are prepared according to the usual methods. The compositions which are subject-matters of the invention are intended for topical application and can in particular constitute a dermatological or cosmetic composition, for example intended for caring for (antiwrinkle, antiageing, moisturizing, antisun protection and the like), treating, cleaning and making up keratinous substances and in particular the skin, lips, hair, eyelashes and nails of human beings.

According to a preferred embodiment of the invention, the composition constitutes a cosmetic composition and is intended for topical application to the skin.

Finally, a subject-matter of the invention is a method for the cosmetic treatment of keratinous substances, such as the skin, including the scalp, keratinous fibres, such as the eyelashes or hair, and/or lips, characterized in that a cosmetic composition as defined above is applied to the said keratinous substances.

The examples which follow will make possible a better understanding of the invention without, however, exhibiting a limiting nature. The amounts shown are as % by weight, unless otherwise indicated.

EXAMPLES

Example 1

| | |
|---|---|
| Copolymer of AMPS and of Genapol T-080 methacrylate (degree of grafting = 7.35%) (Aristoflex SNC from Clariant) | 0.5% |
| Glycerol | 15% |
| Polydimethylsiloxane 10 cSt (DC 200 Fluid from Dow Corning) | 10% |
| Water | q.s. for 100 |

Preparation of the Emulsions:

The amphiphilic copolymer of the invention, supplied in the powder form, is dissolved in water with stirring at 25° C. for 30 minutes; the solution obtained is macroscopically homogeneous. The emulsion is prepared by slow introduction of the oily phase into the aqueous phase with stirring using a homogenizer:
- of Rayneri type equipped with a paddle at a stirring rate of 250 rpm over 20 minutes (emulsion 1).
- of Mixeur type at the maximum stirring rate over 5 minutes (emulsion 2).

The mean size of the oily globules, expressed as apparent mean diameter, the viscosity and the transmission of each composition were measured according to the methods indicated above.

|  | Emulsion 1 | Emulsion 2 |
| --- | --- | --- |
| D [4,3] (μm) | 103.7 | 3.6 |
| Transmission (%) | 95 | 52 |
| Viscosity (Pa · s) Rheomat 180, 25° C., 200 rpm, Spindle 2 | 0.295 | 0.086 |

Emulsion 1 according to the invention is fluid and more translucent than emulsion 2, which exhibits an oily globule size of the order of 3.6 microns: its transmission is 1.8 times greater than that of emulsion 2.

Example 2

| Water | q.s. for 100 |
| --- | --- |
| Copolymer of AMPS and of Genapol T-080 methacrylate (degree of grafting = 7.35%) (Aristoflex SNC from Clariant) | 0.3 |
| Triethanolamine | 0.0026 |
| Preservative | 1 |
| Polysorbate 60 | 0.05 |
| Hydrogenated isoparaffin | 12 |
| Cyclohexasiloxane | 8 |

Procedure:

The amphiphilic copolymer is dissolved in the water, the triethanolamine and the preservative with stirring at 25° C. for 30 minutes; the solution obtained is macroscopically homogeneous. The emulsion is prepared using an in-line IKA turbine. The aqueous phase and the oily phase are introduced simultaneously into the turbine via two different inlets. The rotational speed is set at 3000 rpm and the flow rate is 10 kg/h (emulsion 3). An emulsion 4 is prepared in the same way as emulsion 3, with a final stage of shearing for 2 minutes using a homogenizer of Ultra-Turrax type.

The mean size of the oily globules, expressed as apparent mean diameter, the viscosity and the transmission of each composition are measured according to the methods shown above.

|  | Emulsion 3 | Emulsion 4 |
| --- | --- | --- |
| D [4,3] (μm) | 19.7 | 4.6 |
| Transmission (%) | 54 | 23 |
| Viscosity (Pa · s) Rheomat 180, 25° C., 200 rpm, Spindle 2 | 0.13 | 0.065 |

Emulsion 4, the drop size of which is less than 15 μm, is at least 1.5 times less translucent than emulsion 3, the drop size of which is greater than 15 μm.

Example 3

| Water | q.s. for 100 |
| --- | --- |
| Alkylated (C14/C16) hydroxyethylcellulose (Natrosol 330 plus) | 0.5 |
| Preservative | 1 |
| Hydrogenated isoparaffin | 12 |
| Cyclohexasiloxane | 8 |
| Water | 10.15 |
| Ammonium polyacryloyldimethyl taurate | 0.35 |

Procedure:

The amphiphilic copolymer is dissolved in the water and the preservative with stirring at 25° C. for; the solution obtained is macroscopically homogeneous. The emulsion is prepared using an in-line IKA turbine. The aqueous phase and oily phase are introduced simultaneously into the turbine via two different inlets. The rotational speed is set at 3000 rpm and the flow rate is 10 kg/h. The AMPS gel is introduced afterwards into the vessel with gentle stirring (emulsion 5).

An emulsion 6 is prepared in the same way as emulsion 5, with a final stage of shearing for 2 minutes using a homogenizer of Ultra-Turrax type.

The mean size of the oily globules, expressed as apparent mean diameter, the viscosity and the transmission of each composition are measured according to the methods indicated above.

|  | Emulsion 5 | Emulsion 6 |
| --- | --- | --- |
| D [4,3] (μm) | 19.3 | 12.2 |
| Transmission (%) | 47 | 20 |
| Viscosity (Pa · s) Rheomat 180, 25° C., 200 rpm, Spindle 3 | 1.4 | 0.7 |

Emulsion 5, the drop size of which is less than 15 μm, is 2.3 times less translucent than emulsion 6, the drop size of which is greater than 15 μm.

Example 4

| Water | q.s. for 100 |
| --- | --- |
| Cetyl hydroxyethylcellulose (Polysurf 67 CS) | 0.75 |
| Triethanolamine | 0.061 |
| Citric acid | 0.08 |
| Preservative | 1 |
| Hydrogenated isoparaffin | 12 |
| Cyclohexasiloxane | 8 |

The amphiphilic copolymer is dissolved in the water, the triethanolamine, the citric acid and the preservative with stirring at 25° C.; the solution obtained is macroscopically homogeneous. The oily phase is subsequently slowly introduced into the aqueous phase over 20 minutes using a paddle at a rate of 250 rpm (emulsion 7).

An emulsion 8 is prepared in the same way as emulsion 7, with a final stage of shearing for 2 minutes using a homogenizer of Ultra-Turrax type.

The mean size of the oily globules, expressed as apparent mean diameter, the viscosity and the transmission of each composition are measured according to the methods indicated above.

|  | Emulsion 7 | Emulsion 8 |
|---|---|---|
| D [4,3] (µm) | 41.3 | 6.4 |
| Transmission (%) | 67 | 35 |
| Viscosity (Pa · s) Rheomat 180, 25° C., 200 rpm, Spindle 3 | 0.94 | / |

Emulsion 8, the drop size of which is less than 15 µm, is 1.9 times less translucent than emulsion 7, the drop size of which is greater than 15 µm.

Example 5

| Water | q.s. for 100 |
|---|---|
| Hydroxypropylmethylcellulose stearoxy ether (Sangelose 60L) | 1.2 |
| Preservative | 1 |
| Hydrogenated isoparaffin | 7 |
| Cyclohexasiloxane | 6 |
| Isocetyl stearate | 7 |

The amphiphilic copolymer is dissolved in the water and the preservative with stirring at 25° C.; the solution obtained is macroscopically homogeneous. The oily phase is subsequently slowly introduced into the aqueous phase over 20 minutes using a paddle at a rate of 500 rpm (emulsion 9).

An emulsion 10 is prepared in the same way as emulsion 9, with a final stage of shearing for 2 minutes using a homogenizer of Ultra-Turrax type.

The mean size of the oily globules, expressed as apparent mean diameter, the viscosity and the transmission of each composition are measured according to the methods indicated above.

|  | Emulsion 9 | Emulsion 10 |
|---|---|---|
| D [4,3] (µm) | 25 | 11 |
| Transmission (%) | 14 | 3 |
| Viscosity (Pa · s) Rheomat 180, 25° C., 200 rpm, Spindle 3 | 0.775 | 1.165 |

Emulsion 10, the drop size of which is less than 15 µm, is 4.65 times less translucent than emulsion 9, the drop size of which is greater than 15 µm.

Example 6

| Water | q.s. for 100 |
|---|---|
| Methacrylic acid/methyl acrylate/dimethyl-meta-isopropenylbenzyl isocyanate of ethoxylated alcohol terpolymer (Viscophobe DB 1000) | 2 |
| Triethanolamine | 0.18 |
| Preservative | 1 |
| Hydrogenated isoparaffin | 7 |
| Cyclohexasiloxane | 6 |
| Isocetyl stearate | 7 |

The amphiphilic copolymer is dissolved in the water, the triethanolamine and the preservative with stirring at 25° C.; the solution obtained is macroscopically homogeneous. The oily phase is subsequently slowly introduced into the aqueous phase over 20 minutes using a paddle at a rate of 500 rpm (emulsion 11).

An emulsion 12 is prepared in the same way as emulsion 11, with a final stage of shearing for 2 minutes using a homogenizer of Ultra-Turrax type.

|  | Emulsion 11 | Emulsion 12 |
|---|---|---|
| D [4,3] (µm) | 29.2 | 4.9 |
| Transmission (%) | 59 | 19 |
| Viscosity (Pa · s) Rheomat 180, 25° C., 200 rpm, Spindle 3 | 0.82 | 0.2 |

Emulsion 12, the drop size of which is less than 15 µm, is 3.1 times less translucent than emulsion 11, the drop size of which is greater than 15 µm.

Example 7

| Emulsions 13 and 14 | |
|---|---|
| Water | q.s. for 100 |
| Acrylates/steareth-20 methacrylate copolymer (Aculyn 22) | 3 |
| Triethanolamine | 0.3 |
| Preservative | 1 |
| Hydrogenated isoparaffin | 7 |
| Cyclohexasiloxane | 6 |
| Isocetyl stearate | 7 |

| Emulsions 15 and 16 | |
|---|---|
| Water | q.s. for 100 |
| Acrylates/beheneth-5 methacrylate copolymer (Aculyn 28) | 2 |
| Triethanolamine | 0.2 |
| Preservative | 1 |
| Hydrogenated isoparaffin | 7 |
| Cyclohexasiloxane | 6 |
| Isocetyl stearate | 7 |

The amphiphilic copolymer is dissolved in the water, the triethanolamine and the preservative with stirring at 25° C.; the solution obtained is macroscopically homogeneous. The oily phase is subsequently slowly introduced into the aqueous phase over 20 minutes using a paddle at a rate of 500 rpm (emulsions 13 and 15).

Emulsions 14 and 16 are prepared in the same way as emulsions 13 and 15, with a final stage of shearing for 2 minutes using a homogenizer of Ultra-Turrax type.

|  | Emulsion 13 | Emulsion 14 | Emulsion 15 | Emulsion 16 |
|---|---|---|---|---|
| D [4,3] (µm) | 21.1 | 5.7 | 34.4 | 5.5 |
| Transmission (%) | 48 | 24 | 67 | 25 |
| Viscosity (Pa · s) Rheomat 180, 25° C., 200 rpm, Spindle 3 | 0.305 | 0.14 | 0.520 | 0.21 |

Emulsions 14 and 16, the drop size of which is less than 15 μm, are at least 1.5 times less translucent than emulsions 13 and 15, the drop size of which is greater than 15 μm.

Example 8

| Emulsions 17 and 18 | |
| --- | --- |
| Water | q.s. for 100 |
| Copolymer of AMPS and of Genapol T-080 methacrylate (degree of grafting = 7.35%) (Aristoflex SNC from Clariant) | 0.7 |
| Triethanolamine | 0.006 |
| Preservative | 1 |
| Hydrogenated isoparaffin | 12 |
| Cyclohexasiloxane | 8 |

Procedure:

The amphiphilic copolymer is dissolved in the water, the triethanolamine and the preservative for 30 minutes with stirring at 25° C.; the solution obtained is macroscopically homogeneous. The oily phase is subsequently slowly introduced into the aqueous phase over 30 minutes using a paddle at a rate of 500 rpm (emulsion 17).

An emulsion 18 is prepared in the same way as emulsion 17, with a final stage of shearing for 2 minutes using a homogenizer of Ultra-Turrax type.

The mean size of the oily globules, expressed as apparent mean diameter, the viscosity and the transmission of each composition are measured according to the methods indicated above.

| | Emulsion 17 | Emulsion 18 |
| --- | --- | --- |
| D [4,3] (μm) | 18.6 | 2.5 |
| Transmission (%) | 71 | 12 |
| Viscosity (Pa · s) Rheomat 180, 25° C., 200 rpm, Spindle 2 | 0.365 | 0.178 |

Emulsion 18, the drop size of which is less than 15 μm, is at least 1.5 times less translucent than emulsion 17, the drop size of which is greater than 15 μm.

Example 9

1/ Preparation of a Polystyrene-Block-Poly(Ethyl Acrylate-Stat-Sodium Salt of Acrylic Acid) Diblock Copolymer by Synthesis of a Polystyrene-Block-Poly(Ethyl Acrylate) Diblock Copolymer of the Targeted Mn Values 2000-Block-42000 (q/mol), Followed by 75% Hydrolysis of the Ethyl Acrylate Groups Stage Ia: Preparation of a First Polystyrene Block with a Theoretical Molecular Weight of Approximately 2000 g/mol 3000 g of water, 17.6 g of sodium dodecyl sulphate and 0.290 g of sodium carbonate $Na_2CO_3$ are introduced into the reactor at ambient temperature. The mixture obtained is stirred under nitrogen for 30 minutes. The temperature is subsequently raised to 75° C. and then the addition is carried out of a mixture 1 comprising:

10.00 g of styrene (St),
0.200 g of methacrylic acid (MAA), and
10.42 g of xanthate $(CH_3)(CO_2CH_3)CH-S(C=S)OCH_2CH_3$.

The mixture is brought to 85° C. and then a solution of 1.19 g of sodium persulphate $Na_2S_2O_8$ dissolved in 20.0 g of water is introduced.

After 5 minutes, the addition is begun of a mixture 2 comprising:

90.0 g of styrene (St) and
1.80 g of methacrylic acid (MAA).

The addition is continued for 60 minutes. After complete addition of the various ingredients, the copolymer emulsion obtained is maintained at 85° C. for one hour.

A sample (5 g) is then withdrawn and analysed by steric exclusion chromatography (SEC) in THF. Its measured number-average molecular weight Mn is equal to 2000 g/mol as polystyrene equivalents (calibration by linear polystyrene standards). Its polydispersity index Mw/Mn is equal to 2.0.

An analysis of the sample by gas chromatography reveals that the conversion of the monomers is greater than 99%.

Stage Ib: Preparation of a Second Polyethyl Acrylate) Block with a Theoretical Molecular Weight of Approximately 42 000 g/mol in Order to Obtain a Polystyrene-Block-Polyethyl Acrylate) Diblock Copolymer of the (b) Type The starting material is the emulsified copolymer obtained above in stage Ia, after having withdrawn 5 g therefrom for analysis and without halting the heating. 1.19 g of sodium persulphate $Na_2S_2O_8$, diluted in 50.0 g of water, are introduced continuously over three hours.

Simultaneously, over three hours, the addition is carried out, at 85° C., of a mixture 3 comprising:

200.0 g of water,
2.20 g of sodium carbonate $Na_2CO_3$, and
4.40 g of sodium dodecyl sulphate Simultaneously, the addition is carried out of a mixture 4 comprising:

2100 g of ethyl acrylate (EA), and
42.0 g of methacrylic acid (MAA).

After complete addition of the various ingredients, the copolymer emulsion obtained is maintained at 85° C. for one hour. 4.40 g of tert-butyl benzyl peroxide are then introduced all at once and the addition is begun of a mixture 5 comprising:

2.20 g of erythorbic acid,
50.0 g of water.

The addition is continued for 60 minutes. After complete addition of the various ingredients, the emulsion is cooled to ~25° C. over one hour. A sample (5 g) is then withdrawn and analysed by steric exclusion chromatography (SEC) in THF. Its measured number-average molecular weight Mn is equal to 41 000 g/mol as polystyrene equivalents (calibration with linear polystyrene standards). Its polydispersity index Mw/Mn is equal to 6.

An analysis of the sample by gas chromatography reveals that the conversion of the monomers is greater than 99.8%. The product obtained is a dispersion in water of the copolymer (latex), with a solids content of approximately 41%.

Stage II: Partial Hydrolysis (Targeted at 75%) of the Polyethyl Acrylate) Block of the Copolymer Obtained Above in Stage Ib in Order to Obtain the Polystyrene-Block-Polyethyl Acrylate-Stat-Sodium Salt of Acrylic Acid) Diblock 750 g of water, 250 g of 2-propanol, and 1347 g of emulsified copolymer (c.f. 550 g of copolymer under dry conditions) obtained above in stage Ib are introduced into the reactor at ambient temperature. The mixture obtained is stirred for 15 minutes. The temperature is subsequently raised to 75° C. and then 678 g of sodium hydroxide solution (23.2% by weight solution in water) are added continuously over one hour. After 30 minutes from the beginning of the addition of sodium hydroxide solution, the continuous addition over one hour of 12 g of aqueous hydrogen peroxide solution (30% solution) is begun. After complete addition of the various ingredients, the copolymer solution obtained is maintained at 75° C. for four hours. The reaction mixture is then cooled to 25° C. over one hour.

The product recovered at the end of the reaction is a translucent gel in water with a solids content of approximately 20%.

The copolymer thus obtained exhibits the following characteristics:
Theoretical average molecular weight of the block A: 2000 g/mol
Theoretical average molecular weight of the block B: 30 000 g/mol
Proportion by weight of the block B: 96%
Proportion by weight of the block A: 4%
Amount by weight of units deriving from ethyl acrylate in the block B: 31%

2/ The Following Compositions are Prepared

| Emulsions 19 and 20 | |
|---|---|
| Water | q.s. for 100% |
| Diblock copolymer as synthesized in part 1/above | 3.05%, i.e. 0.48% as AM* |
| Oxyethylenated (20 EO) sorbitan monostearate | 0.05% |
| Preservative | 1% |
| Citric acid | 0.05% |
| Hydrogenated isoparaffin | 7% |
| Cyclohexasiloxane | 6% |
| Isocetyl stearate | 7% |

*Active material

The amphiphilic diblock copolymer is dissolved in the water, the oxyethylenated sorbitan monostearate and the preservative with stirring at 25° C.; the solution obtained is macroscopically homogeneous. The oily phase is subsequently slowly introduced into the aqueous phase over 20 minutes using a paddle at a rate of 500 rpm (emulsion 19). An emulsion 20 is prepared in the same way as emulsion 19, with a final stage of shearing for 2 minutes using a homogenizer of Ultra-Turrax type.

The mean size of the oily globules, expressed as apparent mean diameter, the viscosity and the transmission of each composition are measured according to the methods indicated above.

| | Emulsion 19 | Emulsion 20 |
|---|---|---|
| D [4,3] (μm) | 45.9 | 3.8 |
| Transmission (%) | 60.9 | 11.9 |

Emulsion 20, the drop size of which is less than 15 μm, is 5.1 times less translucent than emulsion 19, the drop size of which is greater than 15 μm.

The invention claimed is:
1. A cosmetic composition for topical application, comprising:
at least one noncrosslinked amphiphilic polymer that is a polymer comprising (a) from 80 to 99 mol % of 2-acrylamido-2-methylpropanesulphonic acid (AMPS) unit of formula (3):

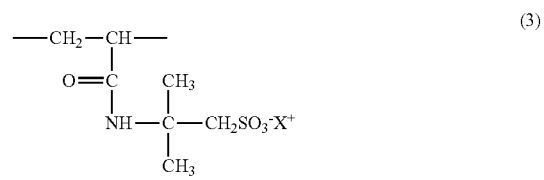

wherein $X^+$ is a proton, an alkali metal cation, an alkaline earth metal cation or the ammonium ion; and
(b) from 1 to 20 mol %, of unit of following formula (3a):

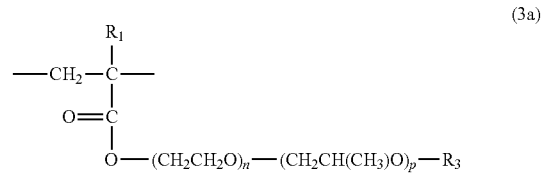

in which n and p are independently a number of moles and vary from 0 to 30, with the proviso that n+p is less than or equal to 30, $R_1$ is a hydrogen atom or a linear or branched $C_1$-$C_6$ alkyl radical and $R_3$ is a linear or branched alkyl group comprising m carbon atoms wherein m is a number from 6 to 30,
wherein
the composition is an oil in water emulsion having an oily phase and an aqueous phase,
the oily phase is dispersed in the aqueous phase,
the composition does not contain a co-emulsifier,
the oily phase is in the form of globules having a mean size ranging from 15 to 500 microns, and
the oily phase is present in the composition in an amount of less than 35% by weight, with respect to the total weight of the composition,
wherein the composition is translucent and has a transmission of light at a wavelength equal to 500 nm, through a sample with a thickness of 50 μm measured using a Carry 600 UV/visible spectrophotometer at a wavelength equal to 500 nm.

2. The composition according to claim 1, wherein the weight-average molar mass of the at least one noncrosslinked amphiphilic polymer is from 10,000 to 10,000,000.

3. The composition according to claim 1, wherein the amount of the at least one noncrosslinked amphiphilic polymer is from 0.01% to 10% by weight, with respect to the total weight of the composition.

4. The composition according to claim 1, wherein the ratio of the amount of oily phase to the amount of the at least one noncrosslinked amphiphilic polymer is from 1 to 200.

5. The composition according to claim 1, wherein the at least one noncrosslinked amphiphilic polymer is a linear polymer or a comb polymer.

6. The composition according to claim 1, wherein the at least one noncrosslinked amphiphilic polymer is partially or completely neutralized.

7. The composition according to claim 1, wherein the amount of oily phase is less than 33% by weight of the total weight of the composition.

8. The composition according to claim 1, wherein the amount of oily phase ranges from 2 to 35% by weight with respect to the total weight of the composition.

9. The composition according to claim 1, wherein the mean size of the globules is from 15 to 300 μm.

10. The composition according to claim 1, wherein the aqueous phase comprises the at least one noncrosslinked amphiphilic polymer.

11. The composition according to claim 1, which further comprises at least one cosmetic adjuvant selected from the group consisting of gelling agents, active principles, preservatives, antioxidants, fragrances, solvents, salts, fillers, sunscreens, coloring materials, basic agents, acidic agents, lipid vesicles, nanocapsules and microcapsules.

12. The composition according to claim 1, wherein the amount of the at least one noncrosslinked amphiphilic polymer is from 0.01% to 10% by weight, with respect to the total weight of the composition, wherein the ratio of the amount of oily phase to the amount of the at least one noncrosslinked amphiphilic polymer is from 1 to 200, wherein the amount of oily phase ranges from 2 to 35% by weight with respect to the total weight of the composition, and wherein the mean size of the globules is from 15 to 300 μm.

13. The composition according to claim 1, in the form of a milk.

14. The composition according to claim 1, in the form of a serum.

15. The composition according to claim 1, having a viscosity of 0.13 to 0.94 Pa.s at 25° C.

\* \* \* \* \*